US009394369B2

(12) United States Patent
Sailor et al.

(10) Patent No.: US 9,394,369 B2
(45) Date of Patent: Jul. 19, 2016

(54) LUMINESCENT POROUS SILICON NANOPARTICLES FOR TARGETED DELIVERY AND IMMUNIZATION

(75) Inventors: Michael J. Sailor, La Jolla, CA (US); Stephen M. Hedrick, Solana Beach, CA (US); Lou Gu, La Jolla, CA (US); Laura Ruff, San Diego, CA (US); Zhengtao Qin, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1107 days.

(21) Appl. No.: 13/342,889

(22) Filed: Jan. 3, 2012

(65) Prior Publication Data
US 2012/0171292 A1 Jul. 5, 2012

Related U.S. Application Data

(60) Provisional application No. 61/429,436, filed on Jan. 3, 2011.

(51) Int. Cl.
| | |
|---|---|
| *A61K 9/18* | (2006.01) |
| *A61K 39/39* | (2006.01) |
| *A61K 39/44* | (2006.01) |
| *A61P 31/04* | (2006.01) |
| *A61P 31/12* | (2006.01) |
| *A61P 31/14* | (2006.01) |
| *A61P 31/16* | (2006.01) |
| *A61P 31/20* | (2006.01) |
| *A61P 31/22* | (2006.01) |
| *A61P 35/00* | (2006.01) |
| *A61P 37/04* | (2006.01) |
| *B82Y 5/00* | (2011.01) |
| *C07K 16/28* | (2006.01) |
| *A61K 9/00* | (2006.01) |
| *A61K 9/14* | (2006.01) |
| *A61K 47/48* | (2006.01) |
| *B82Y 20/00* | (2011.01) |
| *A61K 39/00* | (2006.01) |

(52) U.S. Cl.
CPC ........... *C07K 16/2878* (2013.01); *A61K 9/0019* (2013.01); *A61K 9/143* (2013.01); *A61K 39/39* (2013.01); *A61K 47/48861* (2013.01); *A61K 47/48884* (2013.01); *B82Y 5/00* (2013.01); *B82Y 20/00* (2013.01); *A61K 2039/55516* (2013.01); *A61K 2039/55555* (2013.01); *C07K 2317/75* (2013.01)

(58) Field of Classification Search
None
See application file for complete search history.

(56) References Cited

U.S. PATENT DOCUMENTS

| | | | |
|---|---|---|---|
| 2,674,743 | A | 4/1954 | Gaiser et al. |
| 5,242,950 | A | 9/1993 | Hastings |
| 5,827,729 | A | 10/1998 | Naughton et al. |
| 6,103,479 | A | 8/2000 | Taylor |
| 6,197,575 | B1 | 3/2001 | Griffith et al. |
| 6,218,182 | B1 | 4/2001 | Naughton et al. |
| 6,228,607 | B1 | 5/2001 | Kersten et al. |
| 6,666,214 | B2 | 12/2003 | Canham |
| 6,734,000 | B2 | 5/2004 | Chin et al. |
| 6,770,480 | B1 | 8/2004 | Canham |
| 6,893,816 | B1 | 5/2005 | Beattie |
| 7,312,046 | B2 | 12/2007 | Chin et al. |
| 2002/0072116 | A1 | 6/2002 | Bhatia et al. |
| 2003/0060878 | A1 | 3/2003 | Shadduck |
| 2003/0146109 | A1 | 8/2003 | Sailor et al. |
| 2004/0052867 | A1 | 3/2004 | Canhann |
| 2004/0171143 | A1 | 9/2004 | Chin et al. |
| 2004/0244889 | A1 | 12/2004 | Sailor et al. |
| 2005/0009374 | A1 | 1/2005 | Gao et al. |
| 2005/0042764 | A1 | 2/2005 | Sailor et al. |
| 2005/0101026 | A1 | 5/2005 | Sailor et al. |
| 2005/0181049 | A1 | 8/2005 | Dong et al. |
| 2006/0236436 | A1 | 10/2006 | Li et al. |
| 2006/0255008 | A1 | 11/2006 | Link et al. |
| 2007/0154522 | A1 | 7/2007 | Chow et al. |
| 2008/0102036 | A1 | 5/2008 | Poss et al. |
| 2009/0068214 | A1* | 3/2009 | Qian ............... A61K 39/39 424/186.1 |
| 2009/0208556 | A1 | 8/2009 | Freeman et al. |

FOREIGN PATENT DOCUMENTS

| | | |
|---|---|---|
| AU | 753542 | 2/2000 |
| CA | 2228426 | 2/1997 |
| CA | 2368679 | 11/2000 |
| CN | 99809028.X | 8/2001 |
| CN | 00809693.7 | 8/2002 |
| EP | 1776949 A2 | 4/2007 |
| GB | 9909996.2 | 5/1999 |
| HK | 02100735.8 | 4/2002 |
| KR | 10-2001-7013948 | 11/2000 |
| KR | 10200470143 | 8/2004 |
| KR | 20017001028 | 10/2006 |
| NZ | 509142 | 1/2004 |
| NZ | 515189 | 5/2004 |
| WO | 9706101 | 2/1997 |
| WO | 0066190 | 11/2000 |

(Continued)

OTHER PUBLICATIONS

Wheeler (Salud p'ublica de M'exico, 1997, vol. 39, pp. 283-287).*
Efferson et al (Anticancer research, 2005, vol. 25, pp. 715-24).*
Bachman et al (Journal of Immunology, 2005, vol. 175, pp. 4677-4685).*
Hoffman et al (International Jornal of Cancer, 2005, vol. 115, pp. 98-104).*
Broekhoven et al (Cancer Research, 2004, vol. 64, pp. 4357-4365).*
Zhou et al (Hybridoma, 1999, vol. 18, pp. 471-478).*

(Continued)

*Primary Examiner* — Karen Canella
(74) *Attorney, Agent, or Firm* — Joseph R. Baker, Jr.; Gavrilovich, Dodd & Lindsey LLP

(57) ABSTRACT

The disclosure relates to immunizing agents and devices.

19 Claims, 8 Drawing Sheets

(56) References Cited

FOREIGN PATENT DOCUMENTS

| WO | WO 03040308 | * | 5/2003 |
|---|---|---|---|
| WO | 2004071949 | | 8/2004 |
| WO | 2005034725 | | 4/2005 |
| WO | 2006050221 A2 | | 5/2006 |
| WO | 2009009563 A3 | | 1/2009 |
| WO | 2010096733 A2 | | 8/2010 |

OTHER PUBLICATIONS

Kuratsukuri et al (Urologic Oncology, 2000, vol. 5, pp. 265-273).*
Diwan et al (Journal of Drug Targeting, 2003, vol. 11, pp. 495-507).*
Mercuri et al (Small, 2006, vol. 2, pp. 254-256).*
Tacken et al (Immunobiology, 2006, vol. 211, pp. 599-608).*
Hu et al (Journal of Physical Chemistry B, 2006, vol. 110, pp. 18703-18709).*
Allen, J. W. et al. "Advances in Bioartificial Liver Devices," Hepatology 34:447-455 (2001).
Anglin, Emily J., "Porous silicon in drug delivery devices and materials," Advanced Drug Delivery Reviews 60:1266-1277 (2008).
Baharlou, Simin. International Preliminary Report on Patentability and Written Opinion. International Application No. PCT/US2006/069474. Date of Issuance of this report: Jan. 21, 2010.
Bellet, D. et al., "Controlled Drying: The Key to Better Quality Porous Semiconductors," Advanced Materials 10:487-490 (1998).
Bhatia, S. N. et al., "Controlling cell interactions by micropatterning in cocultures: Hepatocytes and 353 fibroblasts," Journal of Biomedical Materials Research 34:189-199 (1997).
Bhatia, S. N. et al., "Effect of cell-cell interactions in preservation of cellular phenotype: cocultivation of hapatocytes and nonparaenchymal cells," The FASEB Journal 13:1883-1900 (1999).
Bhatia, S. N. et al., "Microfabrication of Hepatocyte/Fibroblast Co-cultures: Role of Homotypic Cell Interactions," Biotechnol. Prog. 14:378-387 (1998).
Bhatia, S. N. et al., "Micropattering Cells in Tissue Engineering," Methods in Molecular Medicine 18:349-363.
Bhatia, S. N. et al., "Tissue Engineering at the Micro-Scale," Biomedical Microdevices 2(2):131-144 (1999).
Campbell, Jenna. "Development of porous silicon microfilters." Undergraduate Thesis. Georgia Institute of Technology (2007).
Canham, L. T. et al., "Derivatized Mesoporous Silicon with Dramatically Improved Stability in Simulated Human Blood Plasma," Advanced Materials 11:1505-1507 (2000).
Chen, C. C. et al., "Size Dependence of Structural Metastability in Semiconductor Nanocrystals," Science 276:398-401 (1997).
Chin, V. et al., "Compatability of Primary Hepatocytes with Oxidized Nanoporous Silicon," Advanced Materials 13:1877-1880 (2001).
Curtis, A. et al., "Topographical control of cells," Biomaterials 18:1573-1583 (1997).
Curtis, A. et al., "Nanotechniques and approaches in biotechnology," Trends in Biotechnology 19:97-101 (2001).
Froner, Elena et al., "Luminescence of porous silicon derived nanocrystals dispersed in water: dependence on initial porous silicon oxidation," J. of Nanoparticle Research 8:1071-1074 (2006).
Ghali, Isis A. International Search Report and Written Opinion. International Application No. PCT/US2005/39177. Date of Mailing of the international search report: May 23, 2007.
Han, Jung Hee. International Search Report and Written Opinion. International Application No. PCT/US2008/069474. Date of mailing of the search report: Jun. 22, 2009.
Harvey, Michael. Examination Report. New Zealand Application No. 583120. Date of Report: Nov. 12, 2010.
Hodgson, J. "ADMET—turning chemicals into drugs," Nature Biotechnology 19:722-726 (2001).
Li, Y. et al., "Polyermer replicas of photonic porous silicon for sensing and drug delivery applications," Science 299:2045-2047 (2003).
Liu, Huiying. The First Office Action. Chinese Application No. 200880106417.9. Date of Mailing Mar. 9, 2011.
Moon, Sun Heup. International Search Report and Written Opinion. International Application No. PCT/US2010/024848. Date of Mailing: Sep. 16, 2010.
Nagamori, S. et al., "Devolopments in bioatificial liver research: concepts, performance, and applications," Journal of Gastroenterology 35:493-503 (2000).
Naff, David M. Nonfinal Office Action. U.S. Appl. No. 10/787,015. Date Mailed: Oct. 10, 2006.
Naff, David M. Final Office Action. U.S. Appl. No. 10/787,015. Date Mailed: Apr. 20, 2007.
Naff, David M. Advisory action (PTOL-303). U.S. Appl. No. 10/787,015. Date Mailed: Jul. 5, 2007.
Naff, David M. Notice of Allowability. U.S. Appl. No. 10/787,015. Date Mailed: Aug. 10, 2007.
Selden, C. et al., "What keeps hepatocytes on the straight and narrow? Maintaining differentiated function in the liver," Gut 44:443-446 (1999).
Steiner, P. et al., "Micromachining applications of porous silicon," Thin Solid Films 255:52-58 (1995).
Stewart, M. P. et al., "Chemical and Biological Applications of Porous Silicon Technology," Advanced Materials 12:859-869 (2000).
Sweryda-Krawiec, Beata et al., "A comparison of porous silicon and silicon nanocrystallite photoluminescence quenching with amines," J. Physic. Chem. 100:13776-13780 (1996).
Webster, T. J. et al., "Enhanced functions of osteoblasts on nanophase ceramics," Biomaterials 21:1803-1810 (2000).
Wittmann-Regis, Agnes. International Preliminary Report on Patentability and Written Opinion. International Application No. PCT/US2005/039177. Date of issuance of this report: Jun. 26, 2007.

* cited by examiner

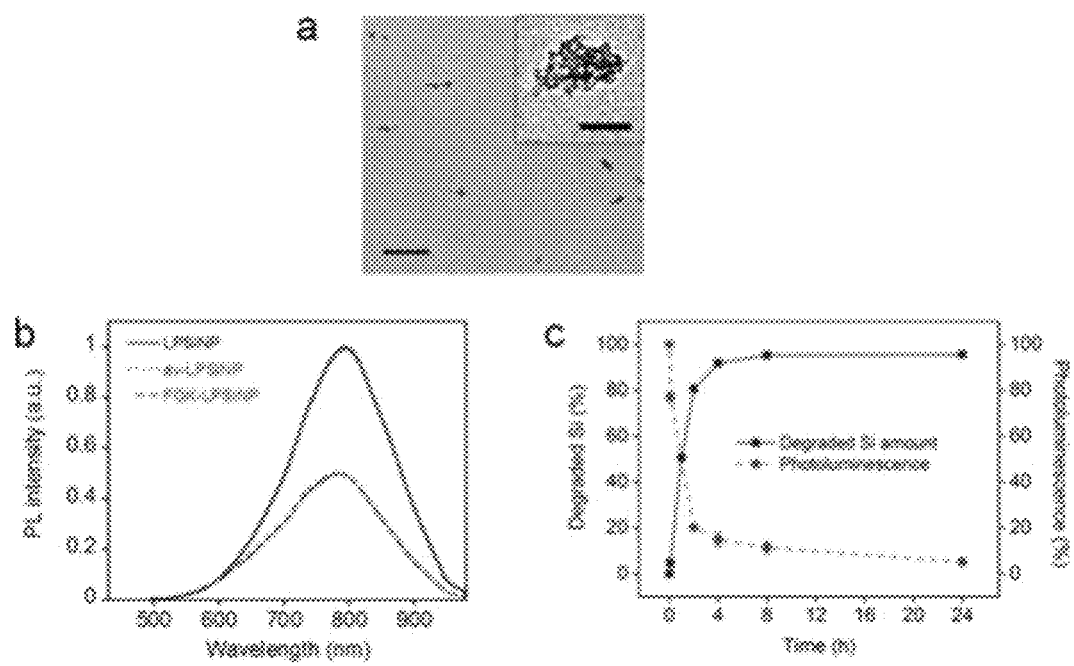
FIGURE 6A-C
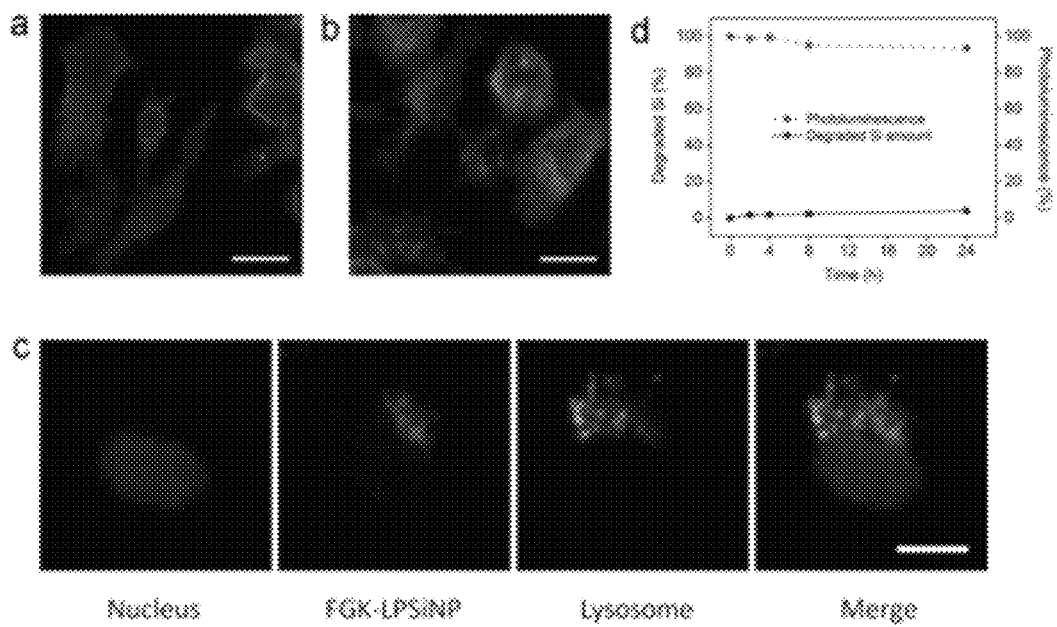
FIGURE 7A-D

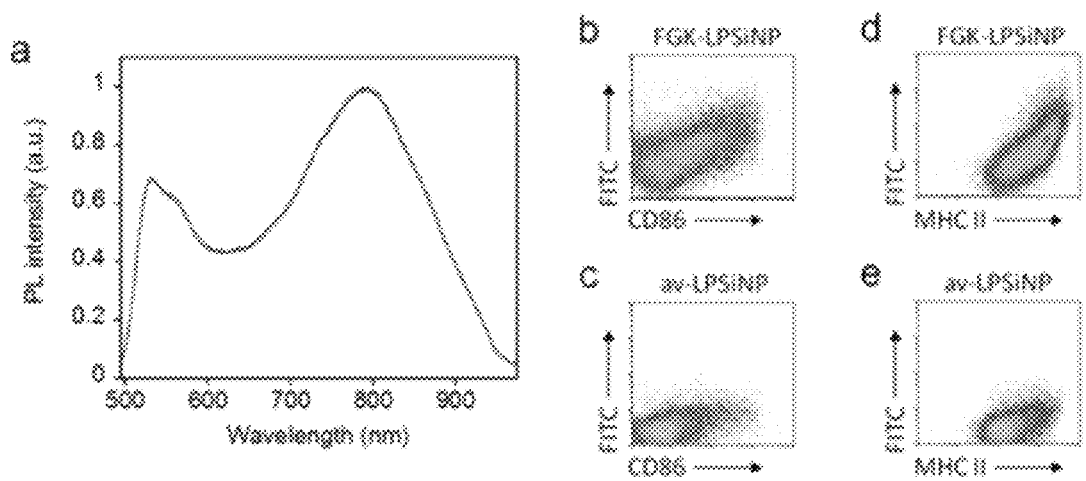
FIGURE 8A-E
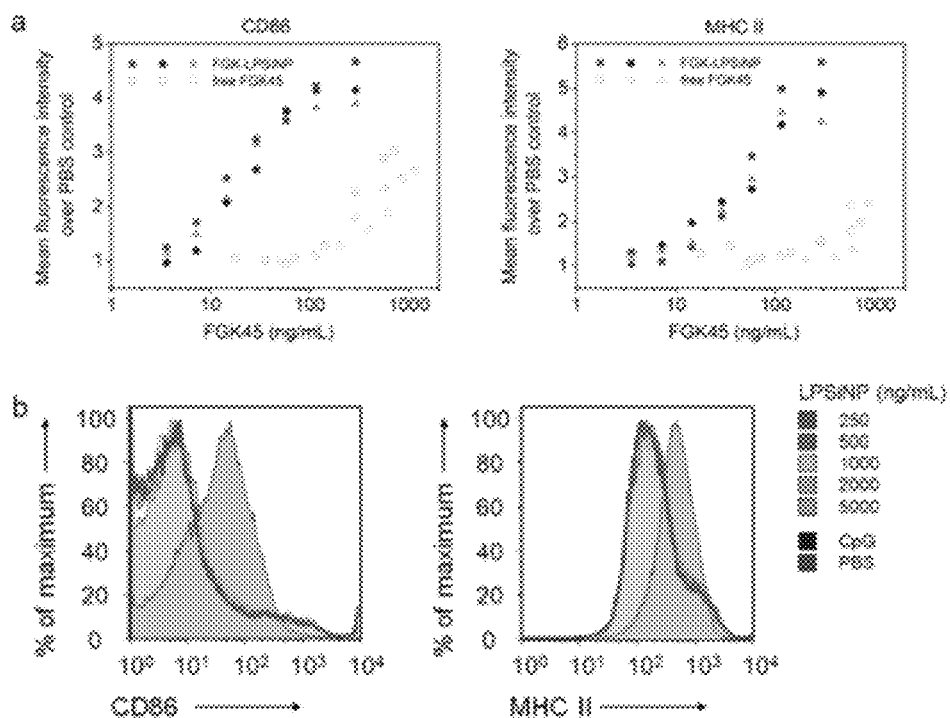
FIGURE 9A-B

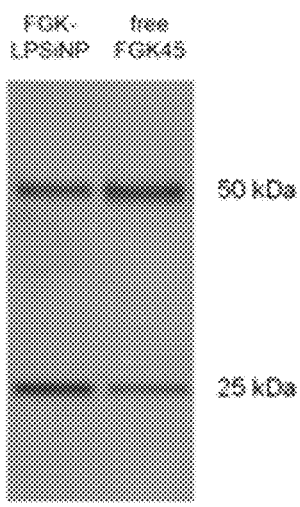
FIGURE 10
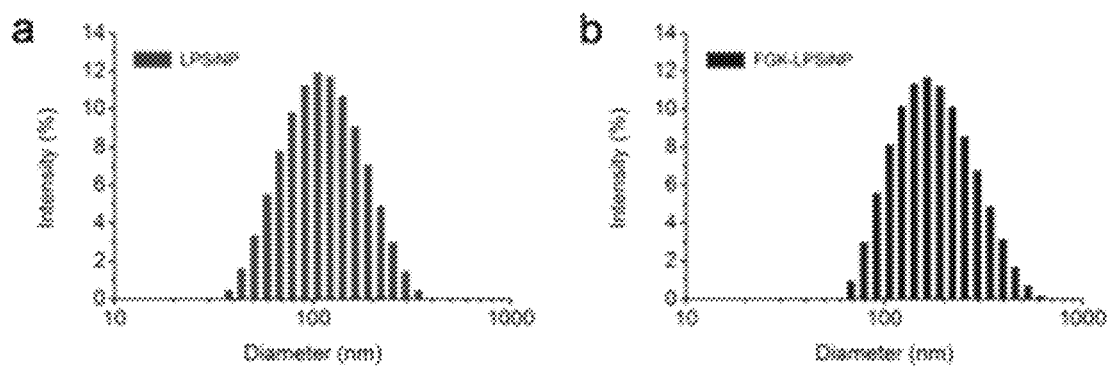
FIGURE 11A-B

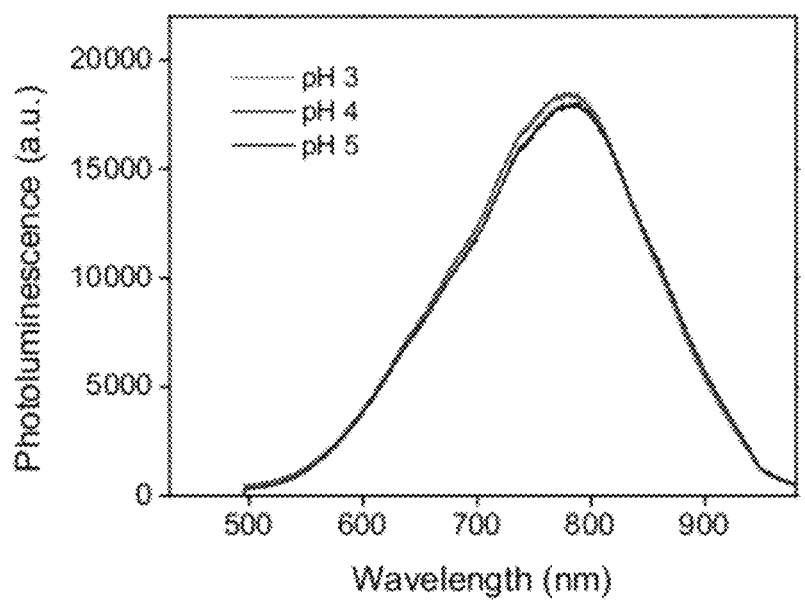
FIGURE 12
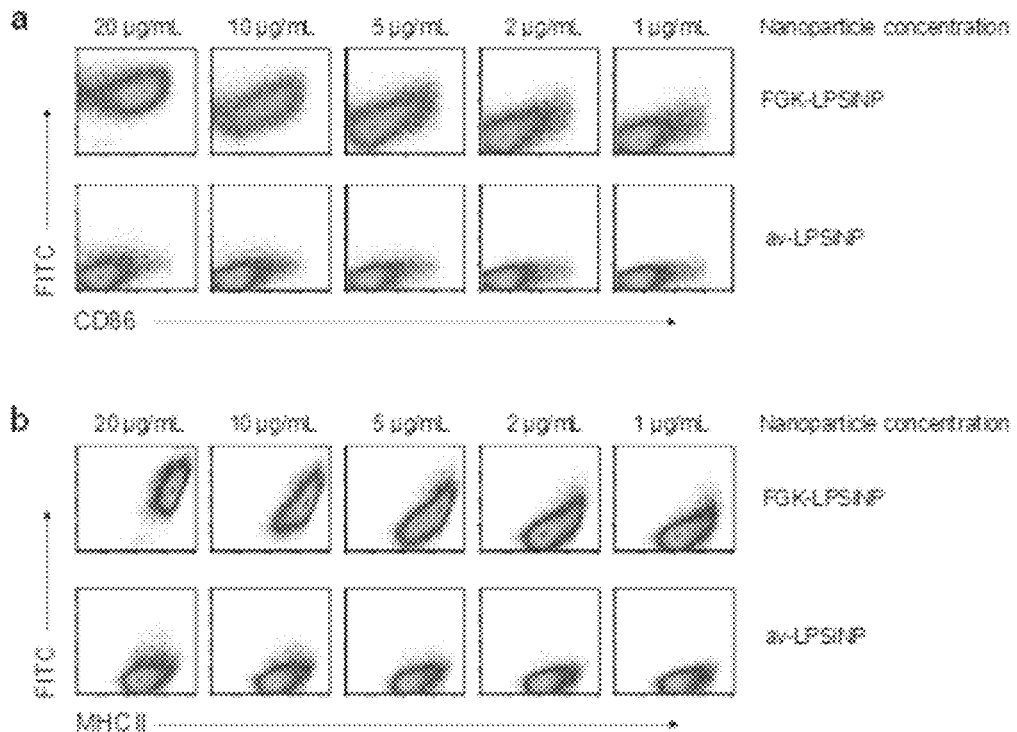
FIGURE 13A-B

LUMINESCENT POROUS SILICON NANOPARTICLES FOR TARGETED DELIVERY AND IMMUNIZATION

CROSS REFERENCE TO RELATED APPLICATIONS

This application claims priority under 35 U.S.C. §119 from Provisional Application Ser. No. 61/429,436, filed Jan. 3, 2011, the disclosure of which is incorporated herein by reference.

STATEMENT AS TO FEDERALLY SPONSORED RESEARCH

The U.S. Government has certain rights in this disclosure pursuant to Grant Nos. AI060536, CA124427, and SUB 5710002667 (CA124427) ARRA awarded by the National Institutes of Health.

TECHNICAL FIELD

The invention relates to delivery systems and, more particularly, to a device, composition and method for immunization.

BACKGROUND

Methods for inducing an immune response in a subject are useful in therapeutics and the prevention of disease and disorders.

SUMMARY

The disclosure provides methods of drug loading, antigen loading and targeting of LPSiNPs.

The disclosure provides porous nanostructures. modified with a composition that modulates immune responses in mammals. More particularly, the disclosure provides a porous nanostructure prepared from elemental silicon and containing a plurality of activator molecules, which together have a greater ability to increase the immune response compared to the same or greater quantity of unbound activator molecules.

The disclosure demonstrates methods and compositions to place antigens into porous Si nanoparticles and to functionalize the nanoparticles with antibodies designed to selectively target and induce a T cell-mediated immune response.

The disclosure provides porous Si nano- and micro-particles useful for antigen/immunogen delivery. The pore size and morphology of Si nanoparticles derived from electrochemically prepared porous Si can be controlled by the preparation conditions. Proper adjustment of pore size and surface chemistry allow the incorporation of various drugs and proteins, and a preparation of photoluminescent porous Si has been demonstrated for imaging of cancer in-vivo and for monitoring delivery of cargo and clearance. Furthermore, porous Si micro- and nanoparticles are biodegradable and have low toxicity which makes them well suited for biological applications.

The disclosure provides a composition comprising (a) a biocompatible porous silicon nanostructure; (b) an antigen presenting cell (APC) stimulating agent adsorbed to the nanostructure; and (c) an antigen loaded into the pores or the porous silicon nanostructure. In one embodiment, the silicon nanostructure comprises a silicon dioxide material. In another embodiment, the nanostructure comprises a particulate size of between about 5 nm and 100 μm. In yet another embodiment, wherein the biocompatible porous nanostructure is non-toxic. In another embodiment, the composition further comprises a targeting moiety linked to the nanostructure's surface. In another embodiment, the targeting moiety is a receptor ligand, receptor or antibody. In a further embodiment, the targeting moiety further comprises stimulating activity that induces APC immunoactivity. In one embodiment, the porous micro- or nanostructure exhibits luminescence when irradiated with light. In another embodiment, the antigen is a cancer cell antigen. In yet a further embodiment, the cancer cell antigen is selected from the group consisting of KS 1/4 pan-carcinoma antigen; ovarian carcinoma antigen (CA125); prostatic acid phosphate; prostate specific antigen; melanoma-associated antigen p97; melanoma antigen gp75; high molecular weight melanoma antigen and prostate specific membrane antigen. In another embodiment, the antigen is a viral antigen. In yet a further embodiment, the viral antigen is an antigenic epitope from hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), human immunodeficiency virus type II (HIV-II) or a combination thereof. In another embodiment, the antigen is a bacterial antigen. In another embodiment, the APC stimulating agent is a CD40 agonist. In a further embodiment, the CD40 agonist is an agonist antibody selected from FGK45, HM40-3, 3/23, 5C3, Mab-89, BE-1, EA5, and M3 monoclonal antibodies. In yet another embodiment, the micro- or nanoparticle is conjugated to a ligand that binds to a CD40, CD205, CD80, CD86, Toll-like receptors (TLR), or the major histocompatibility complex (MHC). In yet another embodiment, the composition induces an immunogenic activity that is at least 1-, 2-, 3-, 4-, 5-, 6-, 7-, 8-, 9-, 10 fold greater than if the same antigen is presented in the absence of the composition. In yet another embodiment, the micro- or nanoparticle of the disclosure comprises granulocyte macrophage colony-stimulating factor (GM-CSF), interferon (IFN)-r, interleukin 15 (IL-15), IL-2, IL-4, or CpG oligodeoxynucleotides.

The disclosure also provides a pharmaceutical comprising any of the compositions described above in combination with a pharmaceutically acceptable carrier.

The disclosure provides a composition comprising a biocompatible porous nanostructure comprising silicon, a plurality of pores wherein the nanostructure has an emission spectrum whose wavelength of maximum intensity lies in the wavelength range from about 500 to about 1000 nm and an excitation spectral maximum in the wavelength range between about 290 to about 700 nm by single photon excitation or about 600 to about 1200 nm by two photon excitation; an antigen within the pores or the nanostructure; and a moiety linked or bound to the particle for targeting to an antigen presenting cell and/or priming/activating the antigen presenting cells.

The disclosure also provides a method of vaccinating a subject comprising contacting the subject with a composition or pharmaceutical as described above, wherein the subject shows increased humoral activity against the antigen.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6A-C shows characterization of FGK45 loaded luminescent porous silicon nanoparticles (FGK-LPSiNP). (A) Transmission electron microscope image of FGK-LPSiNP (inset shows the porous nanostructure of one of the nanoparticles). Scale bar is 1 μm (100 nm for the inset). (B) Photoluminescence (PL) spectra of LPSiNP, av-LPSiNP and FGK-LPSiNP. PL was measured using UV excitation ($\lambda ex=370$ nm). (C) Appearance of dissolved silicon in solution (by ICP-OES) and decrease in photoluminescence intensity from a sample of FGK-LPSiNP (50 μg/mL) incubated in PBS solution at 37° C. as a function of time.

FIG. 7A-D shows dendritic cell uptake of FGK-LPSiNPs. Fluorescence microscope images of mouse bone marrow-derived dendritic cells (BMDC) incubated with (A) LPSiNPs or (B) FGK-LPSiNPs for 1.5 h at 37° C. BMDC were detected by staining with Alexa Fluor 488 conjugated CD11c antibody. FGK-LPSiNPs were detected by their intrinsic visible/near-infrared photoluminescence (red, $\lambda_{ex}=370$ nm and $\lambda_{ex}=720\pm80$ nm). The scale bars are 20 μm. (C) FGK-LPSiNPs distribution in BMDC. BMDC were incubated with FGK-LPSiNP for 1.5 h at 37° C. The lysosomes of the cells were stained with LysoTracker (Invitrogen). Blue and red indicate the cell nucleus and FGK-LPSiNPs, respectively. The scale bar is 10 μm. (D) Degradation of LPSiNPs (50 μg/mL) in pH 4 buffer solution at 37° C. as a function of time.

FIG. 8A-E shows interaction of FGK-LPSiNPs with B cells. (A) Photoluminescence spectrum of LPSiNPs coated with FITC-labeled avidin, showing the emission bands from both the FITC label ($\lambda_{max}$ ~520 nm) and porous silicon ($\lambda_{max}$ ~790 nm). (B)-(E), Flow cytometry data quantifying the level of expression of the B cell activation markers CD86 (B, C) and MHC II (D, E) after incubation with 5 μg/mL of FGK-LPSiNPs (B, D) or av-LPSiNPs (C, E) for 42 h. The nanoparticles used in this experiment were coated with FITC-labeled avidin. The FITC signal from the cells is plotted against the expression level of CD86 (B, C) or MHC II (D, E) after stimulation. FGK-LPSiNPs used here contain 36 μg of FGK45 per milligram of nanoparticles. Note the quantity of FGK45 loaded is smaller when LPSiNPs are coated with FITC conjugated avidin compared with non-labeled native avidin.

FIG. 9A-B shows amplified activation potency of FGK-LPSiNPs compared to free FGK45. (A) Flow cytometry analysis of the expression of B cell activation markers CD86 and MHC II, represented as the relative mean fluorescence intensity of the marker staining, after incubation with either FGK-LPSiNPs or free FGK45 for 42 h at 37° C. The concentration of FGK45 reported for FGK-LPSiNPs is based on the total loading of FGK45 on the nanoparticles (58 μg of FGK45 per mg of nanoparticles). Data are from independent experiments. (B) Flow cytometry histograms of B cell activation markers CD86 and MHC II after incubation with various concentrations of LPSiNPs for 42 h at 37° C. PBS (red shaded) and CpG (blue shaded) were used as negative and positive controls, respectively.

FIG. 10 shows an immunoblot analysis of FGK45 loaded on luminescent porous silicon nanoparticles (LPSiNPs). A western blot used to detect rat IgG (H+L) in FGK-LPSiNPs and free FGK45 is shown. The gel was run under reducing conditions, yielding both heavy (50 kDa) and light (25 kDa) chain antibody bands of FGK45. Antibody that had been loaded on LPSiNPs appears similar to free FGK45.

FIG. 11A-B shows representative hydrodynamic size data. Hydrodynamic size distribution of (A) LPSiNPs and (B) FGK-LPSiNPs obtained by dynamic light scattering. Note that the mean size increases from ~130 nm to ~188 nm due to the attached protein molecules.

FIG. 12 shows photoluminescence spectra of LPSiNPs in acidic buffer solutions at room temperature. The nanoparticles are stable in all three acidic pH values indicated (excitation wavelength 370 nm, emission filter 460 nm longpass).

FIG. 13A-B shows stimulation of B cells using various concentrations of FGK45 loaded LPSiNPs (FGK-LPSiNPs, top row in (A) and (B)) or avidin coated LPSiNPs (av-LPSiNPs, bottom row in (A) and (B)). FGK-LPSiNPs used in this study contain 0.036 mg of FGK45 in 1 mg of nanoparticles. Avidin was conjugated with FITC before coating on the nanoparticles. After 42 h of culture, the FITC signal is only detected from B cells that had been stimulated with FGK-LPSiNPs. The B cells stimulated with FGK-LPSiNPs upregulated the activation markers CD86 (A) and MHC II (B), and the cells with high FITC signal also expressed high levels of CD86 (A) and MHC II (B), which indicates the cells that bound FGK-LPSiNPs were also the ones that upregulated the activation markers.

DETAILED DESCRIPTION

Figure 1:
FIG. 1 is a schematic of the delivery vehicle of the device and the targeting and loading of the vehicle.
Figure 2:
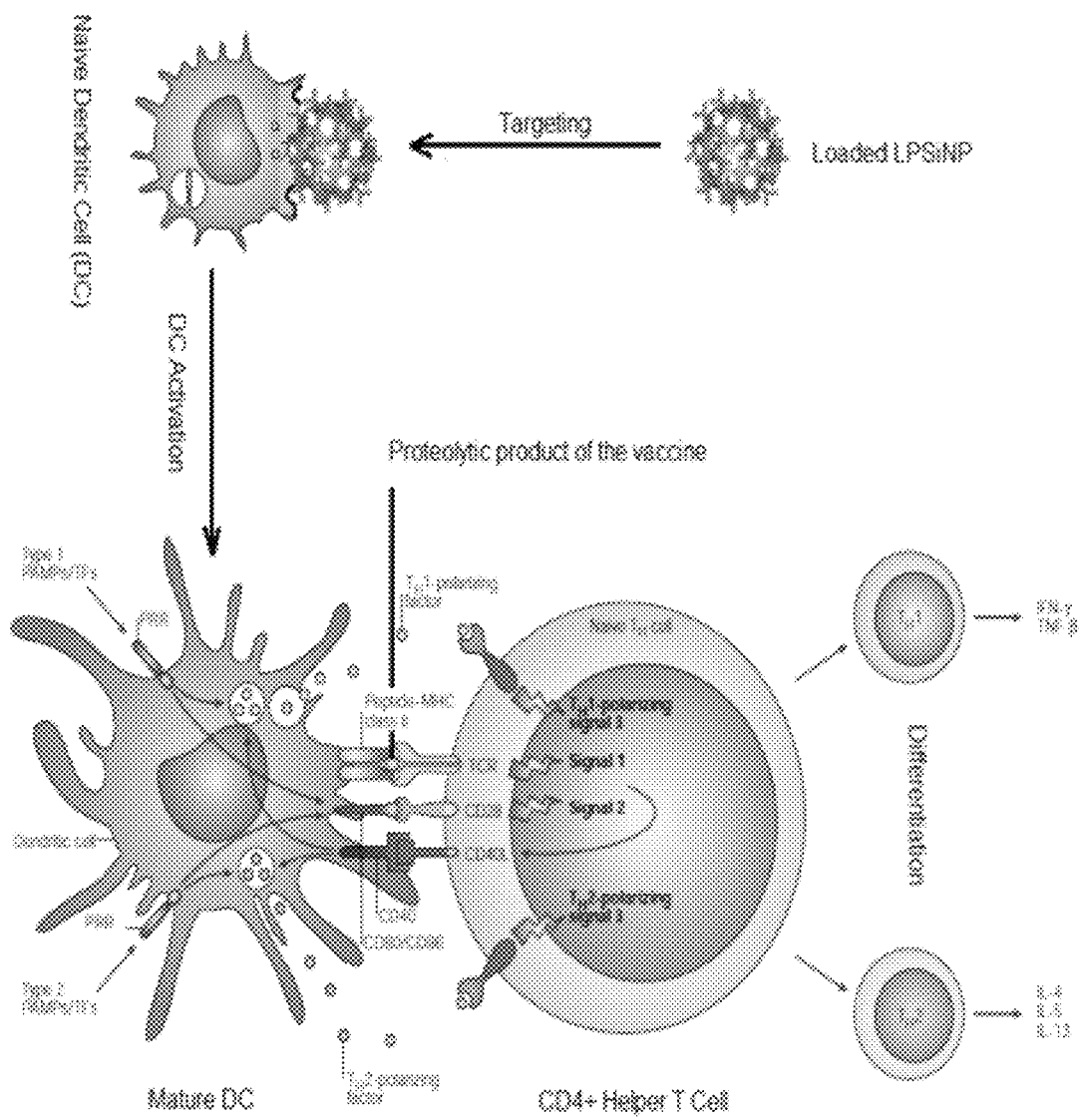
FIG. 2 is a further schematic of the targeting and drawing representing the immune response.
Figure 3:
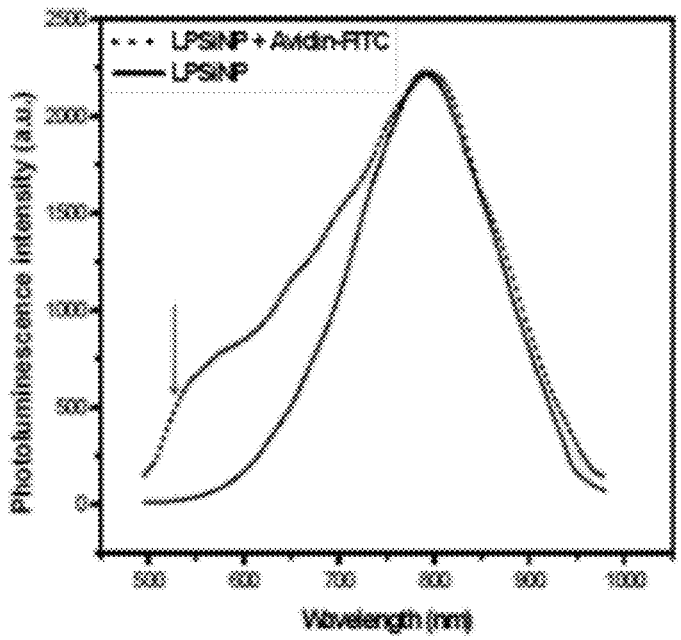
FIG. 3 is shows photoluminescence of LPSiNPs before and after loading of Avidin conjugated to a FITC fluorescent dye.
Figure 4:
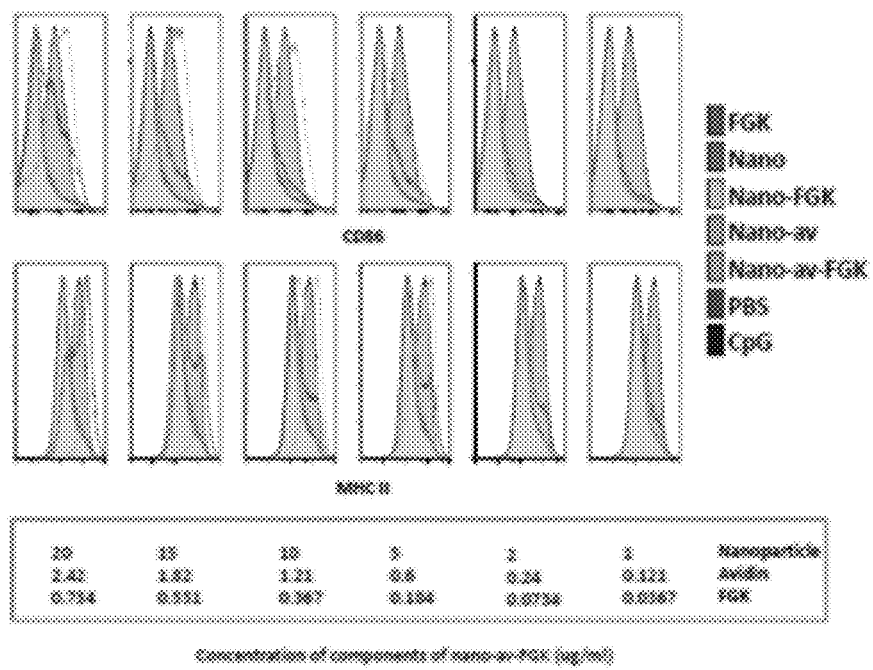
FIG. 4 shows stimulation of B cells in vitro with porous Si nanoparticle complexes.

As used herein and in the appended claims, the singular forms "a," "and," and "the" include plural referents unless the context clearly dictates otherwise. Thus, for example, reference to "a pore" includes a plurality of such pores and reference to "the antigen" includes reference to one or more antigens known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Dendritic cells activate helper T lymphocyte cells and cytotoxic T cells as part of a cascade of events that turn on an immune response in an organism. One of the key interactions is between a dendritic cell receptor known as CD40 and a ligand on the class of helper T lymphocyte cells known as CD4. This interaction induces the dendritic cells to express more CD40, recruiting more CD4 cells and hence amplifying the immune response. The same amplification process can be activated when an antibody to CD40 (anti-CD40 Ab) is introduced; the binding of anti-CD40 Ab to CD40 induces the dendritic cells to express more CD40 on their cellular surface, priming the dendritic cells such that they can better activate CD4 helper T cells. Thus, injection of anti-CD40 Ab can prime the immune system to more effectively combat diseases such as cancer or arthritis. For example, injection of anti-CD40 Ab in mice induces anti-tumor and anti-metastatic effects (Turner et. al, J. Immunol. 166:89-94, 2001). A single CD4 helper T cell can display multiple copies of the CD40 binding ligand on its cellular surface, increasing the probability of one or more favorable binding interactions with a dendritic cell. By contrast, an antibody can only participate in a single binding interaction. This single interaction limits the therapeutic effectiveness of anti-CD40 Ab. The disclosure demonstrates that a micro- or nanoparticle capable of delivering multiple copies of anti-CD40 Ab to a single dendritic cell more effectively mimic this important aspect of the CD4 helper T cell function. This disclosure describes a porous silicon-based micro- or nanoparticle that binds multiple copies of anti-CD40 Ab and activates the immune response (as measured by overexpression of the receptor CD86 and the glucoprotein MHC-II on dendritic cells) 40-fold over the same concentration of free anti-CD40 Ab.

As used herein the term "micro- or nanoparticle", "micro- and/or nanoparticle", "LPSiNP" and "pSiNP" refers to a porous silicon material at least partially comprising silicon dioxide and which have a size range of a few nanometers to a hundred micrometers. Typically the size is about 10-20 nm to 1 micrometer. The geometry may be spherical, oblong, square, rectangular, cuboidal and the like.

The disclosure provides porous silicon micro- and/or nanoparticles (pSiNP) that can carry one or more copies of an immune system modulating molecule or complex that improves the immune response to disease.

Furthermore, in contrast to many micro- and nanomaterials (e.g., carbon nanotubes (CNT), gold nanoparticles (GN), and quantum dots (QD)), pSiNP degrade into renally cleared components in a relatively short period of time with little or no evidence of toxicity. Additionally, in contrast to many biologic-derived delivery systems, the nanoparticles alone (without an added activating complex or molecule) do not induce an immune response.

The disclosure provides porous silicon or porous silicon oxide micro- and/or nanoparticles displaying an extended surface with the capacity to bind a plurality of the same or different molecules or complexes that can modulate an immune response, and they can be engineered to resorb in vivo into benign components that clear renally within a desired time frame.

The disclosure provides a biodegradable porous micro- and/or nanostructure comprising silicon material. In one embodiment, the silicon material comprises a silicon dioxide material. In another embodiment, the silicon material comprises both a silicon and a silicon dioxide material. In another embodiment, the biodegradable/biocompatible porous nanostructure comprises a particulate size of between about 0.01 µm and 1 µm. In yet another embodiment, the biodegradable/biocompatible porous structure can be characterized as non-toxic. In one embodiment, the biodegradable/biocompatible porous structure is coated or encapsulated within a polymeric material that can be engineered to bind the immune system modulating complex(es). In another embodiment, the biodegradable/biocompatible porous structure is coated or encapsulated within a plurality of either streptavidin or avidin protein molecules. In another embodiment, the biodegradable/biocompatible porous structure is coated or encapsulated within a plurality of protein A molecules derived from *Staphylococcus aureus* bacteria. In a further embodiment, the polymeric material is dextran, polylactic acid, polyglycolic acid, collagen, fibrin, copolymers of polylactic acid and polyglycolic acid, and co-polymers of dextran and polylactic acid. In a specific embodiment, the polymeric material is dextran. In yet another embodiment, the biodegradable porous nanostructure is coated with an antibody to CD40.

The disclosure also provides a method of preparing a biodegradable/biocompatible material to deliver stimulatory agents comprising (1) electrochemically etching a silicon wafer to generate a porous structured film; (2) lifting off said porous structured film from the silicon wafer substrate; (3) fracturing the porous film to generate micro- and/or nanoparticles of sizes between 10 nanometers and 1000 nanometers; and (4) activating the structure in an aqueous solution. In one embodiment, the aqueous solution comprises pure water. In one embodiment, the aqueous solution comprises sodium hydroxide, hydrogen peroxide or borate. In a further embodiment, the biodegradable/biocompatible material further comprises loading a molecule or agent that interacts with dendritic cells into the pores or on the micro- or nanostructure. In yet another embodiment, the method further comprises loading an antigen into the pores of the biodegradable/biocompatible material. In yet another embodiment, the method further comprises adsorbing a biocompatible agent to the micro- or nanostructure to increase the half-life or circulatory time in vivo.

The disclosure also provides a pharmaceutical composition comprising a pharmaceutically acceptable carrier and a biodegradable porous nanostructure of the disclosure.

The disclosure provides a composition comprising: a biodegradable/biocompatible porous nanostructure comprising silicon, a plurality of pores of diameters between 1 and 200 nm; and a drug or biologically active material within the pores. In one embodiment, the biodegradable/biocompatible porous structure further comprises a polymeric coating that increases the half-life or circulatory time of the biodegradable porous nanostructure in vivo.

The disclosure provides porous silicon comprising an agent that stimulates/activates antigen presenting cells and one or more antigenic agents (e.g., vaccine). The immunogen/antigenic agent(s) can be used to raise and immune response against any number of viral agents or bacterial agents and cells comprising a cell proliferative disorder having an antigenic marker.

Antigenic agents that are delivered to antigen presenting cells (e.g., dendritic cells) are processed by the cells and presented to other components of the immune system so that the immune system is trained to respond to the antigen: A cellular component that possesses that antigen would then be rejected by the immune system. For example, if an antigen from a polio virus vaccine is delivered to a dendritic cell, then the immune system becomes trained to recognize that antigen. Many vaccines work on this principle of immune system stimulation. Embodiments are disclosed herein that include, for example, delivering antigens to antigen presenting cells (APCS), including, for example, dendritic cells.

The compositions and methods of the disclosure can be used to induce immunity to one or more cancer immunogens, bacterial antigens or viral antigens, comprising providing a porous silicon particle of the disclosure comprising an APC activating agent and one or more immunogens.

The activating agent may be independent of a targeting agent or may be both a targeting agent and an activating agent. For example, targeting an APC (e.g., a dendritic cell) can be used to prime the cell, however, in some embodiments, the agent used to target the APC can also cause activation of the APC (e.g., agonistic antibodies to CD40).

APCs, including leukocytes, may be targeted by making nanoparticles having ligands that recognize targets on the APCs. Observations suggest that targeting the APCs with nanoparticles stimulate the dendritic cells and effectively activate the immune system. The nanoparticles bind the targets, are internalized by the cells, and release the nanoparticle's contents into the cell. Targets are typically receptors that are internalized into the cells by a caveolar pathway. Many suitable targets, including receptors, are known to exist on APCs. Examples of such receptors include, for example, the following receptors, or receptors for: E-selectin, CD3, CD 4, CD8, CD11, CD 14, CD 34, CD 123, CD 45Ra, CD64, E-cadherin, ICAM-1, interleukins, interferons, tumor necrosis factors, E-cadherin, Fc, MCH, CD 36 and other integrins, chemokines, Macrophage Mannose receptor and other lectin receptors, B7, CD's 40, 50, 80, 86 and other costimulatory molecules, Dec-205, scavenger receptors and toll receptors, see also Guermonprez et al. (Annu. Rev. Immunol., 2002). Dendritic cells are considered to be highly effective APCs for initiating MHC-restricted and innate immune responses. Their biology and role in many health and disease states is reviewed in Lipscomb et al. (2001), Physiol. Rev. 82:97-130. In one embodiment, porous silicon is taken up by phagocytosis of macrophages, where antigenic contents of the nanoparticles will be processed and presented as antigens.

The synthesis of LPSiNPs is described herein. Conditions can be optimized to maximize the loading of the proteins streptavidin or avidin. Both proteins were conjugated with a fluorescein (FITC) label, which absorbs at 494 nm and emits at 520 nm. Incorporation into the LPSiNPs was accomplished by electrostatic adsorption.

Biotinylated FGK45 was found to bind to the avidin-loaded nanoparticles. Taking advantage of the strong affinity of streptavidin or avidin for biotin, one embodiment, of the disclosure used biotinylated FGK45 to attach to the avidin surface of LPSiNPs. FGK45 is an antibody for the surface protein CD40, which is expressed on Antigen Presenting Cells (APCs) such as B lymphocytes and dendritic cells. After locating the APCs through the strong binding of CD40 to FGK45, the APCs ingest a vaccine loaded in the LPSiNPs and then present the proteolytic products to T lymphocytes. This presentation activates the naive T cells, stimulating cytotoxic T and B lymphocytes. In addition to providing an enhanced immune response, luminescent Si nanoparticles could provide a means to reveal the underlying pathway.

This disclosure describes the method for using porous silicon nano/micro-particles as adjuvants to modulate immune responses and deliver antigens. Such silicon nano/micro-particles have low toxic, are biodegradable and luminescent. In one embodiment, avidin was physically incorporated onto porous Si nanoparticles, then anti-CD40 antibodies were conjugated with the nanoparticles through avidin-biotin interaction. CD40 is a costimulatory protein found on antigen presenting cells (APCs) and is required for their activation. The binding of its ligands or antibodies to CD40 activates APCs and induces a variety of downstream effects. The disclosure shows that the porous Si nanoparticle construction was about 20 times more potent to stimulate APCs compared to free standing anti-CD40 antibody in vitro. In another embodiment, APCs targeting protein with antigen (anti-DEC205ab/OVA) was co-incorporated into porous Si nanoparticles together with anti-CD40 antibody to form porous Si NanoVaccine. By using the constructed porous Si NanoVaccine, an immunity memory towards the given antigen (ovalbumin here as a model) can be induced in a mouse model.

This disclosure provides useful compositions and methods of porous silicon nanoparticles as adjuvant to more effectively modulate immune responses and deliver antigens for vaccination.

Electrochemically etched porous silicon has exhibited considerable potential for biological applications due to its biocompatibility, biodegradability, encoding property for multiplexed detection, and tunable porous nanostructure for drug delivery. For in vivo use, silicon nanoparticles provide attractive chemical alternatives to heavy metal-containing quantum dots (QDs), which have been shown to be toxic in biological environments.

Silicon is the chemical element that has the symbol Si and atomic number 14. Silicon occasionally occurs as the pure free element in nature, but is more widely distributed as various forms of silicon dioxide (silica) or silicates. Silicon oxide typically refers to a silicon element linked to a single reactive oxygen species (e.g., a radical). Such silicon oxide compounds are useful for the addition of carbon or other desirable elements wherein a bond is formed between the reactive oxygen and the desired element or chemical side chain. Silicon oxides are useful for the formation of hydrogenated silicon oxycarbide (H:SiOC) films having low dielectric constant and a light transmittance. Such Si—O—X (wherein X is any suitable element other than oxygen) compounds are formed using complex reactions including reacting a methyl-containing silane in a controlled oxygen environment using plasma enhanced or ozone assisted chemical vapor deposition to produce the films.

Silicon dioxide refers to the compound $SiO_2$ (sometime referred to as silica). Silicon dioxide is formed when silicon is exposed to oxygen (or air). A thin layer (approximately 1 nm or 10 Å) of so-called 'native oxide' is formed on the surface when silicon is exposed to air under ambient conditions. Higher temperatures and alternate environments are used to grow layers of silicon dioxide on silicon. Silicon dioxide is inert and harmless. When silica is ingested orally, it passes unchanged through the gastrointestinal tract, exiting in the feces, leaving no trace behind. Small pieces of silicon dioxide are equally harmless, so long as they are not large enough to mechanically obstruct the GI tract or fluid flow, or jagged enough to lacerate the GI lining, vessel or other tissue. Silicon dioxide produces no fumes and is insoluble in vivo. It is indigestible, with zero nutritional value and zero toxicity. Silicon dioxide has covalent bonding and forms a network structure. Hydrofluoric acid (HF) is used to remove or pattern silicon dioxide in the semiconductor industry.

Silicon is an essential trace element that is linked to the health of bone and connective tissues. The chemical species of relevance to the toxicity of porous Si are silane ($SiH_4$) and dissolved oxides of silicon; three important chemical reactions of these species are given in Eq. (1)-(3). The surface of porous Si contains Si—H, $SiH_2$, and $SiH_3$ species that can readily convert to silane. Silane is chemically reactive (Eq. (1)) and toxic, especially upon inhalation. Like silane, the native $SiH_x$ species on the porous Si surface readily oxidize in aqueous media. Silicon itself is thermodynamically unstable towards oxidation, and even water has sufficient oxidizing potential to make this reaction spontaneous Eq. (2). The passivating action of $SiO_2$ and Si—H (for samples immersed in HF solutions) make the spontaneous aqueous dissolution of Si kinetically slow. Because of its highly porous nanostructure, oxidized porous Si can release relatively large amounts of silicon-containing species into solution in a short time. The soluble forms of $SiO_2$ exist as various silicic acid compounds with the orthosilicate ($SiO_4^{4-}$) ion as the basic building block (Eq. (3)), and these oxides can be toxic in high doses. Because the body can handle and eliminate silicic acid, the important issue with porous Si-based drug delivery systems is the rate at which they degrade and resorb.

$$SiH_4 + 2H_2O \rightarrow SiO_2 + 4H_2 \quad (1)$$

$$Si + O_2 \rightarrow SiO_2 \quad (2)$$

$$SiO_2 + 2H_2O \rightarrow Si(OH)_4 \quad (3)$$

Surface chemistry plays a role in controlling the degradation properties of porous Si in vivo. After Si is electrochemically etched, the surface is covered with reactive hydride species. These chemical functionalities provide a versatile starting point for various reactions that determine the dissolution rates in aqueous media, allow the attachment of homing species, and control the release rates of drugs. The two most important modification reactions are chemical oxidation (Eq. (2)) and grafting of Si—C species.

The various embodiments provided herein are generally directed to systems and methods for producing a drug delivery device that can deliver cargo for treating or diagnosis of various diseases or disorders including viral and bacterial infections, cancers, tumors and other cell proliferative diseases and disorders, inflammatory diseases and disorders and tissue damage. In addition, the disclosure provides immunization techniques that boost drug delivery or promote drug action or improve immunogen processing associate with a silicon nanoparticle of the disclosure. Such methodology can include activating dendritic cells and other inflammatory cells and stimulating an immune response. In one embodiment, the compositions and methods of the disclosure utilize a porous silicon nanoparticle that comprises an immune activating agent and a vaccine agent. The immune activating agent can be a molecule (e.g., an antibody) that activates a receptor and/or pathway of the immune cells. Once activated the vaccine loaded in or on the porous silicon is then biologically optimized due to immune activation and presented on the antigen presenting cell.

In one embodiment, the disclosure provides a method of generating luminescent porous Si nanoparticles (LPSiNP). The method comprises electrochemical etching of a p-type silicon wafer by application of a constant current density of about 200 mA/cm² in an aqueous HF/ethanol electrolyte. The resulting freestanding film of porous silicon nanostructure is then removed from the crystalline silicon substrate by application of a current pulse of about 4 mA/cm² in an aqueous HF/ethanol electrolyte. The freestanding hydrogen-terminated porous silicon film is subsequently fractured, e.g., by sonication, and then filtered to obtain a desired particle size. Other methods of size selecting the nanoparticles can be performed by centrifugation and chromatography. The nanoparticles are further incubated in deionized (DI) water or other oxidizing aqueous environment such as, for example, a borate aqueous buffer, to activate their luminescence (e.g., in one embodiment in the near-infrared range). Various aqueous buffers that are oxidizing (or neutral to basic) can be used. In some embodiments, an aqueous buffer selected from the group consisting of an aqueous borate buffer, a phosphate buffered saline, and sodium hydroxide. For example, in one embodiment, a borate aqueous buffer is useful. Borates in chemistry are chemical compounds containing boron oxoanions, with boron in oxidation state +3. The simplest borate ion is the trigonal planar, $BO_3^{3-}$, although many others are known. In aqueous solution borate exists in many forms. In acid and near-neutral conditions, it is boric acid, commonly written as $H_3BO_3$ but more correctly $B(OH)_3$. The pKa of boric acid is 9.14 at 25° C. Boric acid does not dissociate in aqueous solution, but is acidic due to its interaction with water molecules, forming tetrahydroxyborate. The resulting LPSiNP can then be further modified or loaded with a desired drug agent or other factor. For example, for dextran-coated LPSiNP (D-LPSiNP), dextran (MW ~20,000, Sigma) is physically absorbed on LPSiNP. Various methods off attaching a coating are known. For example, the process for coating LPSiNPs can be one of, or a combination of processes including physical adsorption, physical absorption, covalent attachment, electrostatic adsorption, precipitation of an insoluble overcoating, electroplating, or electroless plating.

In another embodiment, the LPSiNP materials can be generated by first producing a silicon layer with a pore size range of 2-100 nm (e.g., 5-10 nm, 10-20 nm, 20-30 nm etc.). The silicon layer is etched into the single-crystal silicon substrate in ethanolic HF solution. The entire porous nanostructure is removed from the Si substrate by application of a current pulse. The freestanding hydrogen-terminated porous silicon film is then placed in an aqueous solution and fractured into multi-sized particles by, for example, overnight ultrasonication. The particles can then be filtered if desired (e.g., through a 0.22 μm porous filtration membrane or other size separating device) to obtain porous silicon nanoparticles. For example, separation or size control of LPSiNPs can be achieved by passing the colloidal suspension through physical filters, by centrifugation of the suspension, by electrophoresis, by size exclusion chromatography, or by electrostatic precipitation. The nanoparticles are incubated in an aqueous oxidizing solution to activate their luminescence.

Figure 5:
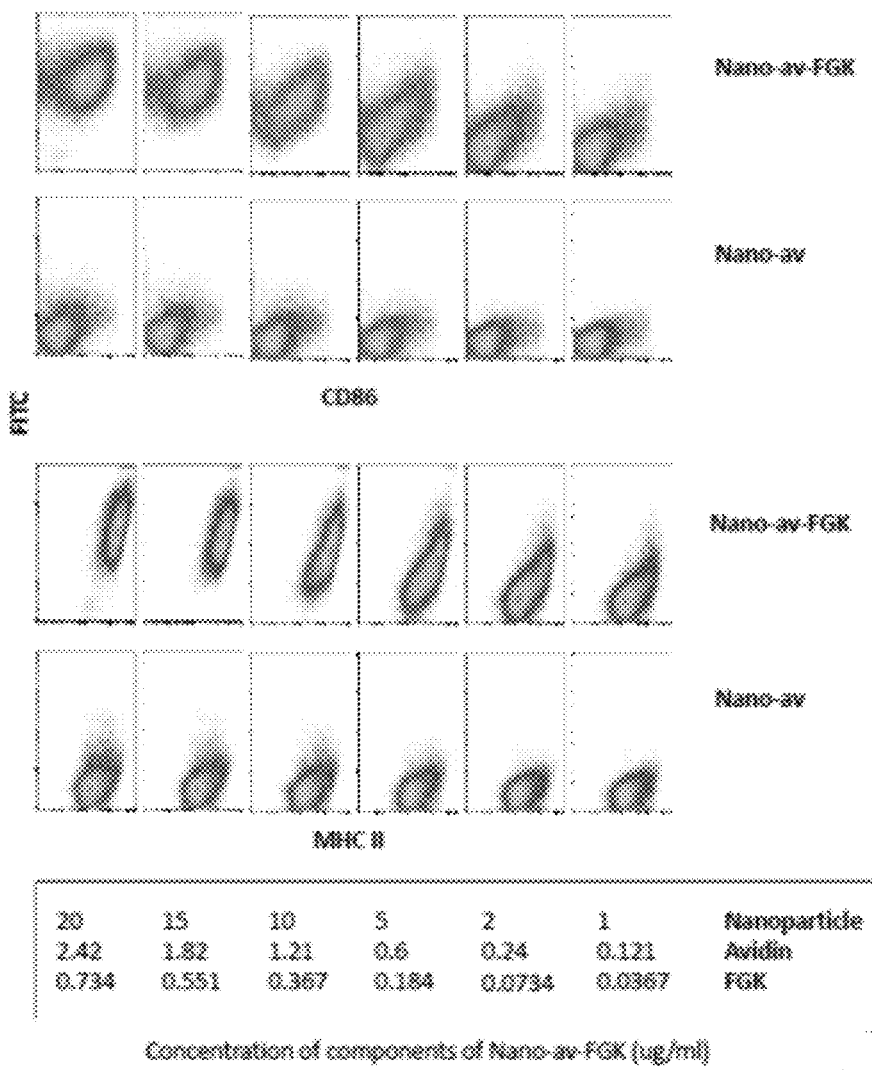
FIG. 5 shows FITC staining of B cells stimulated with porous Si nanoparticles in vitro.

The activation of luminescence is performed in an aqueous solution (see, e.g., FIG. 5). During the activation silicon oxide grows on the hydrogen-terminated porous silicon surface, generating significant luminescence attributed to quantum confinement effects and to defects localized at the $Si/SiO_2$ interface (see, e.g., FIGS. 5 and 6). The preparation conditions of the nanoparticles can be optimized to provide pore volumes and surface areas suitable for loading of therapeutics and for desired in vivo circulation times while maintaining an acceptable degradation rate (FIG. 8-9).

Following is further detail for the production of the LPSiNPs of the disclosure. Photonic crystals are produced from porous silicon and porous silicon/polymer composites, or porous Si film or polymer replica or Si-polymer composite may be generated as a sheet for an exoplant. Pulsed electrochemical etching of a silicon chip produces a multilayered porous nanostructure. A convenient feature of porous Si is that the average pore size can be controlled over a wide range by appropriate choice of current, HF concentration, wafer resistivity, and electrode configuration used in the electrochemical etch. This tunability of the pore dimensions, porosity, and surface area is especially advantageous.

The thickness, pore size, and porosity of a given film is controlled by the current density, duration of the etch cycle, and etchant solution composition. In addition, a porous silicon film can be used as a template to generate an imprint of biologically compatible or bioresorbable materials. The porous silicon film or its imprint possess a sinusoidally varying porosity gradient, providing sharp features in the optical reflectivity spectrum that can be used to monitor the presence or absence of chemicals trapped in the pores. It has been shown that the particles ("smart dust") made from the porous silicon films by mechanical grinding or by ultrasonic fracture still carry the optical reflectivity spectrum.

Porous Si is a product of an electrochemical anodization of single crystalline Si wafers in a hydrofluoric acid electrolyte solution. Pore morphology and pore size can be varied by controlling the current density, the type and concentration of dopant, the crystalline orientation of the wafer, and the electrolyte concentration in order to form macro-, meso-, and micropores. Pore sizes ranging from 1 nm to a few microns can be prepared. The type of dopant in the original silicon wafer is important because it determines the availability of valence band holes that are the key oxidizing equivalents in the reaction shown in FIG. 5. In general the relationships of dopant to morphology can be segregated into four groups based on the type and concentration of the dopant: n-type, p-type, highly doped n-type, and highly doped p-type. By "highly doped," is meant dopant levels at which the conductivity behavior of the material is more metallic than semiconducting. For n-type silicon wafers with a relatively moderate doping level, exclusion of valence band holes from the space charge region determines the pore diameter. Quantum confinement effects are thought to limit pore size in moderately p-doped material. For both dopant types the reaction is crystal face selective, with the pores propagating primarily in the direction of the single crystal. For example, electrochemically driven reactions use an electrolyte containing hydrofluoric acid. Application of anodic current oxidizes a surface silicon atom, which is then attacked by fluoride. The net process is a 4 electron oxidation, but only two equivalents are supplied by the current source. The other two equivalents come from reduction of protons in the solution by surface $SiF_2$ species. Pore formation occurs as Si atoms are removed in the form of $SiF_4$, which reacts with two equivalents of $F^-$ in solution to form $SiF_6^{2-}$.

The porosity of a growing porous Si layer is proportional to the current density being applied, and it typically ranges between 40 and 80%. Pores form at the Si/porous Si interface, and once formed, the morphology of the pores does not change significantly for the remainder of the etching process. However, the porosity of a growing layer can be altered by changing the applied current. The film will continue to grow with this new porosity until the current changes.

This feature allows the construction of layered nanostructures simply by modulating the applied current during an etch. For example, one dimensional photonic crystals consisting of a stack of layers with alternating refractive index can be prepared by periodically modulating the current during an etch.

Stain etching is an alternative to the electrochemical method for fabrication of porous Si powders. The term stain etching refers to the brownish or reddish color of the film of porous Si that is generated on a crystalline silicon material subjected to the process. In the stain etching procedure, a chemical oxidant (typically nitric acid) replaces the power supply used in the electrochemically driven reaction. HF is typically used as an ingredient, and various other additives are used to control the reaction. Stain etching generally is less reproducible than the electrochemical process, although recent advances have improved the reliability of the process substantially. Porous Si powders prepared by stain etch are commercially available.

For in vivo applications, it is often desirable to prepare porous Si in the form of particles. The porous layer can be removed from the Si substrate with a procedure commonly referred to as "electropolishing" or "lift-off." The etching electrolyte is replaced with one containing a lower concentration of HF and a current pulse is applied for several seconds. The lower concentration of HF results in a diffusion limited situation that removes silicon from the crystalline Si/porous Si interface faster than pores can propagate. The result is an undercutting of the porous layer, releasing it from the Si substrate. The freestanding porous Si film can then be removed with tweezers or a vigorous rinse. The film can then be converted into microparticles by ultrasonic fracture. Conventional lithography or microdroplet patterning methods can also be used if particles with more uniform shapes are desired.

The ability to easily tune the pore sizes and volumes during the electrochemical etch is a unique property of porous Si that is very useful for drug delivery applications. Other porous materials generally require a more complicated design protocol to control pore size, and even then, the available pore sizes tend to span a limited range. With electrochemically prepared porous Si, control over porosity and pore size is obtained by adjusting the current settings during etching. Typically, larger current density produces larger pore. Large pores are desirable when incorporating sizable molecules or drugs within the pores. Pore size and porosity is important not only for drug loading; it also determines degradation rates of the porous Si host matrix.

Smaller pores provide more surface area and expose more sites for attack of aqueous media. The smaller porous filaments within the film yield greater dissolution rates, providing a convenient means to control degradation rates of the porous Si host.

The fractionated mixture can be filtered, centrifuged, column sized to obtain a desired nanostructure size. For example, as depicted in FIG. 5, a filter is used to obtain nanostructures smaller than 220 nm.

With its high surface area, porous Si is particularly susceptible to air or water oxidation. Once oxidized, nanophase $SiO_2$ readily dissolves in aqueous media, and surfactants or nucleophiles accelerate the process. Si—O bonds are easy to prepare on porous Si by oxidation, and a variety of chemical or electrochemical oxidants can be used. Thermal oxidation in air tends to produce a relatively stable oxide, in particular if the reaction is performed at >600° C. Ozone oxidation, usually performed at room temperature, forms a more hydrated oxide that dissolves quickly in aqueous media.

Milder chemical oxidants, such as dimethyl sulfoxide (DMSO, Eq. (4)), benzoquenone, or pyridine, can also be used for this reaction. Mild oxidants are sometimes used because they can improve the mechanical stability of highly porous Si films, which are typically quite fragile.

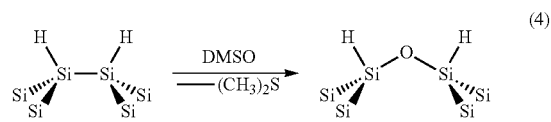

(4)

The mechanical instability of porous Si is directly related to the strain that is induced in the film as it is produced in the electrochemical etching process, and the volume expansion that accompanies thermal oxidation can also introduce strain. Mild chemical oxidants presumably attack porous Si preferentially at Si—Si bonds that are the most strained, and hence most reactive. As an alternative, nitrate is a stronger oxidant, and nitric acid solutions are used extensively in the preparation of porous Si particles from silicon powders by chemical stain etching.

Slow oxidation of the porous Si surface by dimethyl sulfoxide (DMSO), when coupled with dissolution of the newly formed oxide by HF, is a mild means to enlarge the pores in porous Si films. Aqueous solutions of bases such as KOH can also be used to enlarge the pores after etching. Electrochemical oxidation, in which a porous Si sample is anodized in the presence of a mineral acid such as $H_2SO_4$, yields a fairly stable oxide. Oxidation imparts hydrophilicity to the porous structure, enabling the incorporation and adsorption of hydrophilic drugs or biomolecules within the pores. Aqueous oxidation in the presence of various ions including $Ca^{2+}$ generates a calicified form of porous Si that has been shown to be bioactive and is of particular interest for in vivo applications. Calcification can be enhanced by application of a DC electric current.

Carbon grafting stabilizes porous Si against dissolution in aqueous media, but the surface must still avoid the non-specific binding of proteins and other species that can lead to opsonization or encapsulation. Reactions that place a polyethylene glycol (PEG) linker on a porous Si surface have been employed to this end. A short-chain PEG linker yields a hydrophilic surface that is capable of passing biomolecules into or out of the pores without binding them strongly. The distal end of the PEG linker can be modified to allow coupling of other species, such as drugs, cleavable linkers, or targeting moieties, to the material.

The oxides of porous Si are easy to functionalize using conventional silanol chemistries. When small pores are present (as with p-type samples), monoalkoxydimethylsilanes (RO—Si(Me)$_2$—R') can be more effective than trialkoxysilanes ((RO)$_3$Si—R') as surface linkers. This is because trialkoxysilanes oligomerize and clog smaller pore openings, especially when the reagent is used at higher concentrations.

Whereas Si—C chemistries are robust and versatile, chemistries involving Si—O bonds represent an attractive alternative for at least two reasons. First, the timescale in which highly porous $SiO_2$ is stable in aqueous media is consistent with many short-term drug delivery applications—typically 20 min to a few hours. Second, a porous $SiO_2$ sample that contains no additional stabilizing chemistries is less likely to produce toxic or antigenic side effects. If it is desired that the porous Si material be stable in vivo for long periods (for example, an extended release formulation or an in vivo biosensor), Si—C chemistries such as hydrosilylation with end capping or thermal carbonization with acetylene is useful. If a longer-lived oxide matrix is desired, silicon oxides formed at higher temperatures (>700° C.) are significantly more stable in aqueous media than those formed at lower temperatures or by ozone oxidation.

Again, once the smart dust is produced and filtered to a desired size, aqueous oxidation imparts a desired luminescence. In addition, the smart dust can be functionalized to adsorb a ligand binding moiety or other molecules.

For example, CD40 is a co-stimulatory receptor as well as a member of the family of tumor necrosis factor (TNF) receptors found on APCs such as dendritic cells, B cells, and macrophages. Agonistic monoclonal antibodies to CD40 (CD40 mAb) can activate APCs and improve immune responses when used in combination with antigens or vaccines. In addition, CD40 mAb can produce substantial anti-tumor efficacy and can also potentially be used to treat chronic autoimmune inflammation. However, the therapeutically effective dose of CD40 mAb is high and the high dose can result in severe side effects. The disclosure demonstrates that when multiple copies of the CD40 mAb FGK45 are incorporated onto a LPSiNP, the activation potency on B cells is significantly amplified, equivalent to using ~30-40 fold larger concentration of free FGK45.

The LPSiNPs of the disclosure provide a device and method for drug delivery and tissue and disease (e.g., tumor) monitoring. For example, the LPSiNPs of the disclosure have been shown to be a device and method for intravitreal drug delivery that promotes sustained intraocular therapeutic drug levels with minimal invasiveness and elimination of systemic side effects. Impregnation of the porous material may proceed in several ways. The disclosure also provides methods for targeted delivery and analysis of the location of a drug-delivery LPSiNP device of the disclosure.

A drug-delivery LPSiNP device can include any number of candidate drugs depending upon the type of condition, tissue, cancer to be treated. A candidate drug may be "physically" trapped within the pores, or, the pores themselves may be chemically modified to bind the candidate drug. Such a drug can include in the general sense a peptide, polypeptide, small molecule agent, nucleic acid and combinations thereof.

More specifically, "physical trapping" is similar to building a ship in a bottle, where the "ship" is the candidate drug and the "bottle" is the nanometer-scale pores in the porous Si matrix. Small molecules can be trapped in the porous matrix by oxidizing the porous Si around the molecule. Since oxidation of silicon adds two atoms of oxygen per atom of Si to the material, there is a significant increase in volume of the matrix upon oxidation. This has the effect of swelling the pore walls and shrinking the free volume inside the pores, and under the appropriate conditions, molecules present in the pores during oxidation become trapped in the oxide matrix. One aspect of the trapping process is the increased concentration of the active ingredient which occurs during the trapping process. The crystals may present a negatively charged environment and an active ingredient, such as proteins and other drugs, may be concentrated in the crystals to levels much higher than the free concentration of the active ingredient in solution. This can result in 10 to 100 fold or more increase in active ingredient concentration when associated with a crystal. The oxidizing can be performed at repeated intervals by performing layered oxidation. For example, a biological agent or drug can be trapped in the pores by controlled addition of oxidants. Oxidation of the freshly prepared (hydride-terminated) porous Si material results in an effective shrinking of the pores. This occurs because the silicon oxide formed has a larger volume than the Si starting material. If a drug is also present in the solution that contains the oxidant, the drug becomes trapped in the pores.

Furthermore the porous silicon oxide can comprise a higher concentration of a biological agent or drug than a non-oxidized Si hydride material.

The free volume in a porous Si film is typically between 50 and 80%. Oxidation should reduce this value somewhat, but the free volume is expected to remain quite high. Most of the current drug delivery materials are dense solids and can deliver a small percentage of drug by weight. The amount of drug that can be loaded into the porous Si material is expected to be much larger than, for example, surface-modified nanoparticles or polylactide (PLA) polymers.

Various approaches to load a molecular payload into a porous Si host have been explored, and they can be grouped into the following general categories: covalent attachment, physical trapping, and adsorption.

Covalent attachment provides a convenient means to link a biomolecular capture probe to the inner pore walls of porous Si for biosensor applications, and this approach can also be used to attach drug molecules, peptides and the like. As described elsewhere herein, linking a biomolecule via Si—C bonds tends to be a more stable route than using Si—O bonds due to the susceptibility of the Si—O species to nucleophilic attack.

One of the more common approaches is to graft an organic molecule that contains a carboxyl species on the distal end of a terminal alkene. The alkene end participates in the hydrosilylation reaction, bonding to the Si surface and leaving the carboxy-terminus free for further chemical modification. One such linker molecule is undecylenic acid, which provides a hydrophobic 10 carbon aliphatic chain to insulate the linker from the porous Si surface. The drug payload can be attached directly to the carboxy group of the alkene, or it can be further separated from the surface with a PEG linker. Due to the stability of the Si—C bond, hydrosilylation is good way of attaching a payload to porous Si. The payload is only released when the covalent bonds are broken or the supporting porous Si matrix is degraded.

In yet another embodiment, electrostatic adsorption can be used, essentially an ion exchange mechanism that holds molecules more weakly. Electrostatics is a useful means to affect more rapid drug delivery, as opposed to covalent or physical trapping approaches that release drug over a period of days, weeks, or months.

The affinity of a porous Si particle for a particular molecule can be controlled with surface chemistry. The surface of oxidized porous Si has a point of zero charge at a pH of around 2, and so it presents a negatively charged surface to most aqueous solutions of interest. At the appropriate pH, porous $SiO_2$ spontaneously adsorbs positively charged proteins such as serum albumin, fibrinogen, protein A, immunoglobulin G (IgG), or horseradish peroxidase, concentrating them in the process. Accordingly, agonist receptor ligands or agonist antibodies can be adsorbed to the surface of the LPSiNP to target and activate APC cells to combine activation of APCs with immunogen presentation.

Porous Si can also be made hydrophobic, and hydrophobic molecules such as the steroid dexamethasone or serum albumin can be loaded into these nanostructures. Hydrophilic molecules can also be loaded into such materials with the aid of the appropriate surfactant. The native hydride surface of porous Si is hydrophobic. Such techniques have been used for short-term loading and release. Because water is excluded from these hydrophobic surfaces, aqueous degradation and leaching reactions tend to be slow. The grafting of alkanes to the surface by hydrosilylation is commonly used to prepare materials that are stable in biological media; this stability derives in large part from the ability of the hydrophobic moieties to locally exclude water or dissolved nucleophiles.

A delivery LPSiNP device can include any number of candidate antigens depending upon the type of condition, tissue, disease or disorder to be treated. A candidate antigen may be "physically" trapped within the pores, or, the pores themselves may be chemically modified to bind the candidate drug.

Other drugs or "active ingredient" that can be used with the smart dust of the disclosure include any one or any combination of the following, but are not limited to, anti-angiogenic compounds such as bevacizumab, ranibizumab, pegaptanib, and other compounds in the angiogenic cascade. Anti-cancer drugs such as, for example, chemotherapeutic compounds and/or derivatives thereof (e.g., 5-fluorouracil, vincristine, vinblastine, cisplatin, doxyrubicin, adriamycin, tamoxifen, etc.). Also included are glucocorticosteroids such as dexamethasone, triamcinolone acetonide, fluocinolone acetonide and other comparable compounds in the corticosteroid and cortisene families. Also included are compounds such as antacids, anti-inflammatory substances, coronary dilators, cerebral dilators, peripheral vasodilators, anti-infectives, psychotropics, anti-manics, stimulants, anti-histamines, laxatives, decongestants, vitamins, gastrointestinal sedatives, anti-diarrheal preparations, anti-anginal drugs, vasodilators, anti-arrhythmics, anti-hypertensive drugs, vasoconstrictors and migraine treatments, anti-coagulants and anti-thrombotic drugs, analgesics, anti-pyretics, hypnotics, sedatives, anti-emetics, anti-nauseants, anti-convulsants, neuromuscular drugs, hyper- and hypoglycemic agents, thyroid and anti-thyroid preparations, diuretics, anti-spasmodics, uterine relaxants, mineral and nutritional additives, anti-obesity drugs, anabolic drugs, erythropoietic drugs, anti-asthmatics, bronchodilators, expectorants, cough suppressants, mucolytics, drugs affecting calcification and bone turnover and anti-uricemic drugs. Specific drugs include gastro-intestinal sedatives such as metoclopramide and propantheline bromide; antacids such as aluminum trisilicate, aluminum hydroxide, ranitidine and cimetidine; anti-inflammatory drugs such as phenylbutazone, indomethacin, naproxen, ibuprofen, flurbiprofen, diclofenac, dexamethasone, prednisone and prednisolone; coronary vasodilator drugs such as glyceryl trinitrate, isosorbide dinitrate and pentaerythritol tetranitrate; peripheral and cerebral vasodilators such as soloctidilum, vincamine, naftidrofuryl oxalate, co-dergocrine mesylate, cyclandelate, papaverine and nicotinic acid; anti-infective substances such as erythromycin stearate, cephalexin, nalidixic acid, tetracycline hydrochloride, ampicillin, flucloxacillin sodium, hexamine mandelate and hexamine hippurate; neuroleptic drugs such as flurazepam, diazepam, temazepam, amitryptyline, doxepin, lithium carbonate, lithium sulfate, chlorpromazine, thioridazine, trifluperazine, fluphenazine, piperothiazine, haloperidol, maprotiline hydrochloride, imipramine and desmethylimipramine; central nervous stimulants such as methylphenidate, ephedrine, epinephrine, isoproterenol, amphetamine sulfate and amphetamine hydrochloride; antihistamic drugs such as diphenhydramine, diphenylpyraline, chlorpheniramine and brompheniramine; anti-diarrheal drugs such as bisacodyl and magnesium hydroxide; the laxative drug, dioctyl sodium sulfosuccinate; nutritional supplements such as ascorbic acid, alpha tocopherol, thiamine and pyridoxine; anti-spasmodic drugs such as dicyclomine and diphenoxylate; drugs affecting the rhythm of the heart such as verapamil, nifedipine, diltiazem, procainamide, disopyramide, bretylium tosylate, quinidine sulfate and quinidine gluconate; drugs used in the treatment of hypertension such as propranolol hydrochloride, guanethidine monosulphate, methyldopa, oxprenolol hydrochloride, captopril and hydralazine; drugs used in the treatment of migraine such as ergotamine; drugs affecting coagulability of blood such as epsilon aminocaproic acid and protamine sulfate; analgesic drugs such as acetylsalicylic acid, acetaminophen, codeine phosphate, codeine sulfate, oxycodone, dihydrocodeine tartrate, oxycodeinone, morphine, heroin, nalbuphine, butorphanol tartrate, pentazocine hydrochloride, cyclazacine, pethidine, buprenorphine, scopolamine and mefenamic acid; anti-epileptic drugs such as phenyloin sodium and sodium valproate; neuromuscular drugs such as dantrolene sodium; substances used in the treatment of diabetes such as tolbutamide, disbenase glucagon and insulin; drugs used in the treatment of thyroid gland dysfunction such as triiodothyronine, thyroxine and propylthiouracil, diuretic drugs such as furosemide, chlorthalidone, hydrochlorthiazide, spironolactone and triamterene; the uterine relaxant drug ritodrine; appetite suppressants such as fenfluramine hydrochloride, phentermine and diethylproprion hydrochloride; anti-asthmatic and bronchodilator drugs such as aminophylline, theophylline, salbutamol, orciprenaline sulphate and terbutaline sulphate; expectorant drugs such as guaiphenesin; cough suppressants such as dextromethorphan and noscapine; mucolytic drugs such as carbocisteine; anti-septics such as cetylpyridinium chloride, tyrothricin and chlorhexidine; decongestant drugs such as phenylpropanolamine and pseudoephedrine; hypnotic drugs such as dichloralphenazone and nitrazepam; anti-nauseant drugs such as promethazine theoclate; haemopoietic drugs such as ferrous sulphate, folic acid and calcium gluconate; uricosuric drugs such as sulphinpyrazone, allopurinol and probenecid; and calcification affecting agents such as biphosphonates, e.g., etidronate, pamidronate, alendronate, residronate, teludronate, clodronate and alondronate.

Insofar as the disclosure contemplates including a virtually unlimited number of drugs, in vitro pharmacokinetic studies can be used to determine the appropriate configuration of the porous silicon film and its dust for each drug. The drug conjugated LPSiNPs can be monitored once delivered to a subject. Light intensity from the LPSiNPs can be measured using a low power spectrophotometer. Using such methods the half-life, delivery and collection of drugs and/or LPSiNPs can be monitored.

The luminescent spectrum used in particle identification can readily be measured with inexpensive and portable instrumentation such as a CCD spectrometer or a diode laser interferometer. Removal of a drug from the LPSiNPs can result in a change in the luminescence of the LPSiNPs as a wavelength shift in the spectrum. Such techniques can be used to enable noninvasive sensing through opaque tissue.

The LPSiNP of the disclosure can be formulated for in vitro and in vivo administration using techniques known in the art.

The LPSiNP materials of the disclosure can be formulated in pharmaceutically acceptable carrier. Pharmaceutically acceptable carriers useful for administration to a cell, tissue or subject are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physicochemical characteristics of the therapeutic agent and on the route of administration of the composition, which can be, for example, orally or parenterally such as intravenously, and by injection, intubation, or other such method known in the art. The pharmaceutical composition also can contain a second (or more) compound(s) such as a diagnostic reagent, nutritional substance, toxin, or therapeutic agent, for example, a cancer chemotherapeutic agent and/or vitamin(s).

The prepared anti-CD40 antibody loaded porous Si nanoparticles could be used to activate APCs and possible downstream effects; Anti-CD40 antibody and anti-DEC205ab/Ovalbumin loaded porous Si nanoparticles are shown to achieve vaccination towards the given antigen (ovalbumin here as a model). The incorporated ligands to costimulatory protein is not limited to anti-CD40 ab. Other ligands with immune modulatory effects could also be potentially conjugated to porous Si micro/nano-particles through this method. The APCs targeting protein is not limited to anti-DEC205ab. Anti-MHC ab, anti-TLR2 Ab can also be used for better targeting of APCs and more effective vaccination (or immune tolerance). Other antigens besides ovalbumin could be delivered as well (conjugated or unconjugated forms).

While the disclosure provides for use with a virtually unlimited number of antigenic candidates, several exemplary antigens are listed below.

The disclosure generally discusses immunization in the context of prophylactic methods of protection. Thus, a method of immunizing includes methods of protecting an individual from pathogen challenge or occurrence or proliferation of specific cells as well as autoimmune disease.

The methods and compositions of the disclosure are applicable to a wide range of species, e.g., humans, non-human primates, horses, cattle, pigs, sheep, goats, dogs, cats, rabbits, guinea pigs, hamsters, rats, and mice. While the disclosure herein primarily relates to uses of the methods of the disclosure to immunize humans, the methods of the disclosure can be applied to veterinary medical uses too. It is within the scope of the disclosure to provide methods of immunizing non-human as well as human individuals against pathogens and protein specific disorders and diseases. The methods of the disclosure can be particularly useful for mammalian species including human, bovine, ovine, porcine, equine, canine and feline species.

The isolation of potentially immunogenic peptides from MHC molecules is known in the art (See, Falk, et al., 1990, Nature 348:248-251; Rotzsche, et al., 1990, Nature 348:252-254; Elliott, et al., 1990, Nature 348:191-197; Falk, et al., 1991, Nature 351:290-296; Demotz, et al., 1989, Nature 343:682-684; Rotzsche, et al., 1990, Science 249:283-287; the disclosures of which are incorporated herein by reference). Briefly, MHC-peptide complexes may be isolated by a conventional immunoaffinity procedure. The peptides then may be eluted from the MHC-peptide complex by incubating the complexes in the presence of about 0.1% TFA in acetonitrile. The eluted peptides may be fractionated and purified by reverse phase HPLC.

The amino acid sequences of the eluted peptides may be determined either by manual or automated amino acid sequencing techniques known in the art. Once the amino acid sequence of a potentially protective peptide has been determined, the peptide may be synthesized in any desired amount using conventional peptide synthesis or other protocols known in the art.

Peptides having the same amino acid sequence as isolated peptides may be synthesized by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile.

Antigens or antigenic portions thereof can be selected for use as antigenic molecules to generate an immune response (immunogenicity). To determine the ability of a molecule to induce an immune reaction and/or to generate/react with antibodies, various techniques are known in the art. To determine immunogenicity or antigenicity by detecting binding to antibody, various immunoassays known in the art can be used including, but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in vivo immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immunoelectrophoresis assays, and the like. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Methods known in the art for detecting binding in an immunoassay and are envisioned for use. In one embodiment for detecting immunogenicity, T cell-mediated responses can be assayed by standard methods, e.g., in vitro cytoxicity assays or in vivo delayed-type hypersensitivity assays.

Potentially useful antigens or derivatives thereof for use as antigenic molecules can also be identified by various criteria, such as the antigen's involvement in neutralization of a pathogen's infectivity or reduction in disease progression or spread (wherein it is desired to treat or prevent infection by such a pathogen) (Norrby, 1985, Summary, in Vaccines BS, Lerner, et al. (eds.), Cold Spring Harbor Laboratory, Cold Spring Harbor, N.Y., pp. 388-389), type or group specificity, recognition by patients' antisera or immune cells, and/or the demonstration of protective effects of antisera or immune cells specific for the antigen. In addition, where it is desired to treat or prevent a disease caused by pathogen, the antigen's encoded epitope typically displays a small or no degree of antigenic variation in time or amongst different isolates of the same pathogen.

Where it is desired to prevent a cell proliferative disorder such as cancer, known tumor-specific antigens or fragments or derivatives thereof are used to produce a protective immunity in offspring by immunizing the mother. For example, such tumor specific or tumor-associated antigens include, but are not limited to, KS 1/4 pan-carcinoma antigen (Perez and Walker, 1990, J. Immunol. 142:3662-3667; Bumal, 1988, Hybridoma 7(4):407-415); ovarian carcinoma antigen (CA125) (Yu, et al., 1991, Cancer Res. 51(2):468-475); prostatic acid phosphate (Tailer, et al., 1990, Nucl. Acids Res. 18(16):4928); prostate specific antigen (Henttu and Vihko, 1989, Biochem. Biophys. Res. Comm. 160(2):903-910; Israeli, et al., 1993, Cancer Res. 53:227-230); melanoma-associated antigen p97 (Estin, et al., 1989, J. Natl. Cancer Inst. 81(6):445-446); melanoma antigen gp75 (Vijayasardahl, et al., 1990, J. Exp. Med. 171(4):1375-1380); high molecular weight melanoma antigen (Natali, et al., 1987, Cancer 59:55-63) and prostate specific membrane antigen.

Where it is desired to prevent viral diseases, molecules comprising epitopes of known viruses are used. For example, such antigenic epitopes may be prepared from viruses including, but not limited to, hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II).

Where it is desired to prevent bacterial infections, molecules comprising epitopes of known bacteria are used. For example, such antigenic epitopes may be prepared from bacteria including, but not limited to, mycobacteria *rickettsia*, mycoplasma, *neisseria* and *legionella*.

Where it is desired to prevent protozoal infections, molecules comprising epitopes of known protozoa are used. For example, such antigenic epitopes may be prepared from protozoa including, but not limited to, *leishmania*, kokzidioa, and *trypanosoma*.

Where it is desired to prevent parasitic infections, molecules comprising epitopes of known parasites are used. For example, such antigenic epitopes may be from parasites including, but not limited to, chlamydia and *rickettsia*.

The nano- or microparticles can be further modified for targeting to a particular cell. Such targeting molecules are known and can be bound to the surface of the particle using biotin and avidin, chemical modifications and the like.

EXAMPLES

Preparation of FGK45 Loaded Luminescent Porous Silicon Nanoparticles (FGR-LPSiNPs)

LPSiNPs were first prepared using a previously described method (see, e.g., US Pat. Publ. 20100196435A1). In brief, (100)-oriented p-type single-crystal Si wafers (0.8-1.2 mΩ cm, Siltronix) were electrochemically etched in an electrolyte containing aqueous 48% hydrofluoric acid and ethanol in a 3:1 ratio. The resulting porous Si films were lifted from the Si substrate, fractured by ultrasound and filtered through a 0.22 μm membrane. Finally, the photoluminescence of the nanoparticles were activated by soaking in deionized water for 14 d. To prepare FGK-LPSiNP, an avidin coating was first applied. A 1 mL aliquot of an aqueous dispersion of 0.2 mg of LPSiNP was mixed with a 0.08 mL aliquot of water containing 0.04 mg of avidin (Thermo Fisher Scientific, Inc.). The mixture was stirred for 1 h at room temperature, rinsed with water three times by centrifugation. The particles were resuspended in water to 0.2 mg/mL and were then mixed with a 0.045 mL aliquot of water containing 0.022 mg of biotin conjugated FGK45 (Enzo Life Sciences, Inc.). The mixture was stirred for 1-h at room temperature, rinsed with water three times by centrifugation to remove any excess FGK45. The supernatant of each wash was combined and the quantity of excess FGK45 in the supernatant was measured by micro BCA (bicinchoninic acid) protein assay (Thermo Fisher Scientific, Inc.) to calculate the quantity of FGK45 loaded on LPSiNP.

Nanoparticle Characterization.

Transmission electron micrographs (TEM) were obtained with a FEI Tecnai G2 Sphera. Dynamic light scattering (Zetasizer Nano ZS90, Malvern Instruments) was used to determine the hydrodynamic size of the nanoparticles. The photoluminescence (PL, $\lambda ex=370$ nm and 460 nm long pass emission filter) spectra of LPSiNP or FGK-LPSiNP were obtained using a Princeton Instruments/Acton spectrometer fitted with a liquid nitrogen-cooled silicon charge-coupled device (CCD) detector.

In Vitro Degradation of FGR-LPSiNP.

A series of samples containing 0.05 mg/mL of FGK-LPSiNP in 1 mL of PBS solution or pH 4.0 buffer solution were incubated at 37° C. An aliquot of 0.5 mL of solution was removed at different time points and filtered with a centrifugal filter (30,000 Da molecular weight cut-off, Millipore, inc.) to remove undissolved LPSiNP. 0.4 mL of the filtered solution was diluted with 5 mL HNO3 (2% (v/v)) and subjected to analysis by inductively coupled plasma optical emission spectroscopy (ICP-OES, Perkin Elmer Optima 3000DV). The decrease in PL of the above samples over time was also monitored.

Mice.

C57BL/6 mice were maintained in specific pathogen-free facilities at the University of California, San Diego: Animal protocols were approved by the Institutional Animal Care and Use Committee.

Cell Uptake of FGR-LPSiNP.

Mouse bone marrow-derived dendritic cells (BMDC) were prepared and harvested on day 8 for use in microscopy experiments. BMDC (40,000 cells per well) were seeded into 8-well chamber glass slides (Millipore, inc.) and cultured overnight. The cells were washed with DMEM (Dulbecco's Modified Eagle Medium) once and incubated with 0.05 mg/mL LPSiNP or FGK-LPSiNP in DMEM for 1.5 hours at 37° C. The cells were washed 3 times with DMEM and incubated with Alexa Fluor 488 conjugated CD11c antibody (clone N418, eBioscience—all antibodies are from eBioscience unless otherwise indicated; 1 µg/ml) in DMEM for 10 min to visualize the BMDC. The cells were then rinsed three times with PBS, fixed with 4% paraformaldehyde for 20 min and then observed with a Nikon Eclipse LV150 fluorescence microscope fitted with a thermoelectrically cooled CCD camera (CoolSNAP HQ2, Photometrics). An excitation wavelength of 360 nm and an emission filter with a bandpass at 720±80 nm were used to image the near-IR photoluminescence of the nanoparticles.

In Vitro Stimulation of B Cells.

Single-cell suspensions of C57BL/6 splenocytes were prepared and subjected to RBC lysis using ACK lysis buffer. B cells were sorted out via CD43 magnetic bead depletion. Sorted cells were plated at $2 \times 10^5$ cells/well and incubated with LPSiNP, av-LPSiNP, FGK-LPSiNP, free agonistic anti-CD40 (clone FGK45), PBS, or CpG for 42 h at 37° C.

Flow Cytometry.

Approximately 1-2 million cells were resuspended in HBSS 1% FCS, incubated for 15 min at 4° C. with anti-mouse FCincu-III, and stained with fluorescently conjugated antibodies for 20 min at 4° C. For particles using avidin-FITC, cells were stained with MHC II biotin (M5/114.15.2), washed with HBSS 1% FCS, stained with streptavidin PerCP, CD86 PE (GL1) and B220 Allophycocyanin (RA3-6B2) and analyzed by flow cytometry. For particles using non-labeled avidin, cells were stained with B220 FITC, CD86 PE and MHC II Allophycocyanin and analyzed by flow cytometry.

Immunoblot Analysis.

FGK-LPSiNPs and FGK45 were diluted in LDS sample buffer and reducing agent (Invitrogen), incubated at 80° C. for 10 min, loaded on a 4-12% Bis-Tris gel (Invitrogen) and run under reducing conditions. The gel was then transferred to PVDF membrane and a western blot was performed to detect rat IgG. Briefly, the membrane was blocked in 5% milk in TEST for 30 min, probed with goat anti-rat IgG (H+L) HRP (Southern Biotech, diluted 1:10,000 in 5% milk in TBST) for 60 min, washed three times with TBST, prepared with ECL Plus substrate (Amersham Biosciences) and signal was detected on a Typhoon 9400 variable mode imager (Amersham Biosciences).

Photoluminescence Measurement of LPSiNPs in Acidic Buffer Solutions.

LPSiNPs were suspended in pH 3, 4 or 5 buffer solutions (VWR International, LLC) at a concentration of 0.05 mg/mL. The photoluminescence (PL, $\lambda ex=370$ nm and 460 nm long pass emission filter) spectra of LPSiNPs in various pH buffer solutions were obtained using a Princeton Instruments/Acton spectrometer fitted with a liquid nitrogen-cooled silicon charge-coupled device detector.

LPSiNPs were prepared by electrochemical etch of highly doped p-type single-crystal Si wafers in an electrolyte consisting of aqueous hydrofluoric acid and ethanol, lift-off of the porous layer, ultrasonic fracture, filtration of the resulting nanoparticles through a 0.22 µm filter membrane, and finally activation of luminescence by treatment in an aqueous solution as described above. To incorporate FGK45 onto the nanoparticles, the LPSiNPs were first coated with avidin by physisorption (av-LPSiNPs). Biotinylated FGK45 was then conjugated to the nanoparticles through the strong biotin-avidin binding interaction (FGK-LPSiNPs), FIG. 1a. Approximately 0.058 mg of FGK45 was loaded per milligram of LPSiNPs, as measured by bicinchoninic acid (BCA) protein assay. The structure of FGK45 loaded on nanoparticle-FGK45 construct was also confirmed by gel electrophoresis and immunoblotting (FIG. 10). The FGK-LPSiNPs appeared similar to LPSiNPs in the transmission electron microscope (TEM) images (FIG. 6a), but the mean hydrodynamic size measured by dynamic light scattering (DLS) increased from ~130±10 nm of LPSiNPs to ~188±15 nm after protein attachment (FIG. 10).

The intrinsic photoluminescence from the silicon nanostructures in FGK-LPSiNPs under ultraviolet excitation appeared in the near-infrared region of the spectrum ($\lambda max=790$ nm), similar to the non-loaded LPSiNPs. However, the intensity of photoluminescence was somewhat lower from the protein-coated formulation (FIG. 6b). In a physiologically relevant aqueous solution of phosphate buffered saline (PBS) at pH 7.4 and 37° C., the FGK-LPSiNP construct was observed to degrade within 24 h (FIG. 6c). The degradation was tracked by monitoring disappearance of the photoluminescence signal, which decreased gradually upon dissolution of the quantum confined silicon nanostructure, and by appearance of free silicic acid in solution (by inductively coupled plasma-optical emission spectroscopy, ICP-OES) (FIG. 6c).

The FGK-LPSiNPs were more readily taken up by APC compared to bare LPSiNPs. When cultured with mouse bone marrow-derived dendritic cells (BMDC), LPSiNPs showed limited (but still detectable) presence in the cells (FIG. 7a); in contrast, BMDC incubated with FGK-LPSiNPs under the same conditions showed much higher uptake of nanoparticles (FIG. 7b). It has been reported that CD40 ligand and agonistic antibodies can induce CD40 endocytosis upon binding. The increased uptake of FGK-LPSiNPs can be attributed to the binding of FGK45 to CD40 expressed on the BMDC. By following the near-infrared photoluminescence spectrum of the nanoparticles, FGK-LPSiNPs were found presented outside of the lysosomes of the dendritic cells (FIG. 7c). This finding is consistent with previous reports that various types of silicon or silica based nanomaterials can escape from lysosomes and distribute inside the cytosol. Although LPSiNPs are expected to degrade within a few hours at pH 7.4 due to dissolution of the protective oxide coating, they are much more stable in acidic environments such as in the interior of lysosomes (FIG. 11). In pH 4 buffer solution, less than 5% of the nanoparticles dissolved over 24 h (FIG. 7d).

The interaction of FGK-LPSiNPs with B cells using a 4-color flow cytometer was then examined. The nanoparticles in this experiment contained avidin labeled with fluorescein isothiocyanate (avidin-FITC). The resulting construct emits both in the green (from the FITC label) and in the near-infrared (from the silicon nanostructure) when excited with ultraviolet light (FIG. 8a). B cells sorted from mouse splenocytes were incubated with FGK-LPSiNPs or av-LPSiNPs and then analyzed by flow cytometry. After 42 h of culture, the FITC signal was only detected from B cells that had been exposed to FGK-LPSiNPs (FIG. 8b-e). B cells incubated with FGK-LPSiNPs also displayed upregulated expression of the activation markers CD86 and major histocompatibility complex class II (MHC II), the response expected from APCs activated by FGK45 (FIG. 8b-e). Furthermore, the extent of activation induced by FGK-LPSiNPs is concentration dependent. B cells cultured with higher concentrations of FGK-LPSiNPs showed higher activation levels (FIG. 12). When exposed to a low concentration of FGK-LPSiNPs, not all of the B cells were activated, as indicated by the wide distribution of the fluorescence intensity from the cells in the flow cytometry dot plots (FIG. 8b, 8d). However, the population of B cells that displayed high FITC signals also expressed high levels of CD86 and MHC II, indicating that the cells bound with nanoparticles were the ones that upregulated their activation markers (FIG. 8b, 8d). In contrast, B cells cultured with various concentrations of av-LPSiNP all showed low FITC signals and low activation marker levels (FIG. 13).

Multivalency is one of the notable advantages of using nanomaterials for biomedical applications. For example, studies using nanoparticles as cancer diagnostic and therapeutic agents have shown that when multiple copies of tumor targeting ligand are displayed on an individual nanoparticle, its tumor targeting efficiency can be significantly enhanced. This enhancement is generally ascribed to the multivalent effect which is also observed in many natural processes such as antibody interactions and clotting interactions. To determine if multivalency plays a strong role in the activation potency of the agonistic antibody to APCs, B cells were cultured with either FGK-LPSiNPs or an equivalent concentration of free FGK45 and analyzed the cells by flow cytometry. Both FGK-LPSiNPs and free FGK45 activated B cells, and the activation level of the cells correlated with the concentration of FGK45 (FIG. 9a). However, at a given total concentration of FGK45 antibody, FGK-LPSiNPs showed substantially higher activation potency than free FGK45. Activated B cells upregulated CD86 and MHC II to a detectable level when cultured with FGK-LPSiNPs containing as little as ~3.6-7.2 ng/mL of FGK45; whereas a similar level of B cell activation was only observed when the concentration of free FGK45 was ≥140-200 ng/mL (FIG. 9a). Comparison of the titration curves of FGK-LPSiNPs and free FGK45 revealed that the B cell activation potency of FGK45 in the FGK-LPSiNP constructs is equivalent to using ~30-40 fold larger concentration of free FGK45 (FIG. 9a). This was truly surprising and unexpected.

Figure 14:
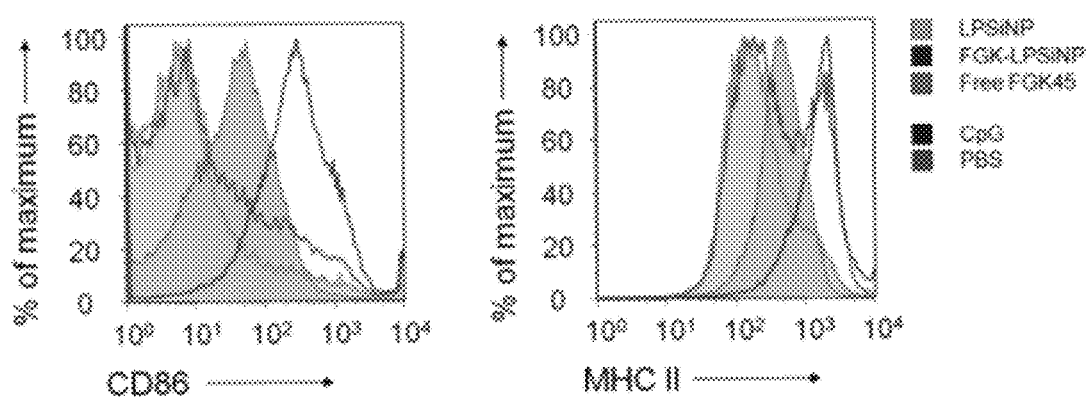
FIG. 14 shows there is no CD86 or MHC II upregulation of B cells incubated with LPSiNP. Flow cytometry histograms of B cell activation markers CD86 and MHC II after incubation with 5 μg/mL of LPSiNPs (green curve), 5 μg/mL of FGK-LPSiNPs containing 0.29 μg of FGK45 (maroon curve), or 0.29 μg of free FGK45 (magenta curve) for 42 h at 37° C. PBS (red shaded) and CpG (blue shaded) were used as negative and positive controls, respectively.

To test if the enhancement of APC activation is caused by the uncoated porous silicon nanomaterial itself, B cells were cultured with various concentrations of LPSiNPs as control experiments. No upregulation of CD86 or MHC II was observed at all tested LPSiNP concentrations (up to 5000 ng/mL, equivalent to the highest concentration of FGK-LPSiNPs used in the stimulation study). This suggests that the amplification induced by the FGK-LPSiNP construct results from enhancement of the agonistic antibody's intrinsic function rather than an immune response from the nanomaterial itself (FIG. 9b and FIG. 14). The very low stimulation of APC by LPSiNPs is attributed to their primarily inorganic chemical composition; their chemical structure and biodegradation products possess little similarity to natural pathogens or other "danger signals" normally presented to the immune system.

This study represents the first example of a nanoparticle that amplifies APC activation potency of agonistic CD40 antibody. In addition to the enhancement effect, the inert inorganic composition and biodegradable property of LPSiNPs could overcome some of the disadvantages of lipid or polymer-based materials for immunotherapy applications. Their intrinsic photoluminescence also provides a means to monitor the degradation of LPSiNPs and track their interaction with the immune system. The amplifying effect and the synthetic versatility of the silicon nanomaterial provide a promising means to develop immunomodulators or nanovaccines.

A number of embodiments of the invention have been described. Nevertheless, it will be understood that various modifications may be made without departing from the spirit and scope of the invention. Accordingly, other embodiments are within the scope of the following claims.

What is claimed is:
1. A composition comprising:
 (a) a biocompatible porous silicon micro- or nanostructure that exhibits luminescence when irradiated with light;
 (b) an antigen presenting cell (APC) stimulating agent adsorbed to the micro- or nanostructure; and
 (c) an antigen loaded into the pores of the porous micro- or nanostructure.
2. The composition of claim 1, wherein at least a portion of the silicon micro- or nanostructure comprises a silicon dioxide material.
3. The composition of claim 1, wherein the micro- or nanostructure comprises a particulate size of between about 5 nm and 100 µm.
4. The composition of claim 1, wherein the biocompatible porous micro- or nanostructure is non-toxic.
5. The composition of claim 1, further comprising a targeting moiety linked to the micro- or nanostructure surface.
6. The composition of claim 5, wherein the targeting moiety is a receptor ligand, receptor or antibody.
7. The composition of claim 5, wherein the targeting moiety further comprises stimulating activity that induces APC immunoactivity.
8. The composition of claim 1, wherein the antigen is a cancer cell antigen.
9. The composition of claim 8, wherein the cancer cell antigen is selected from the group consisting of KS 1/4 pan-carcinoma antigen; ovarian carcinoma antigen (CA125), prostatic acid phosphate; prostate specific antigen; melanoma-associated antigen p97; melanoma antigen gp75; high molecular weight melanoma antigen and prostate specific membrane antigen.
10. The composition of claim 1, wherein the antigen is a viral antigen.
11. The composition of claim 10, wherein the viral antigen is an antigenic epitope from hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, arbovirus, hantavirus, coxsackie virus, mumps virus, measles virus, rubella virus, polio virus, human immunodeficiency virus type I (HIV-I), human immunodeficiency virus type II (HIV-II) or a combination thereof.
12. The composition of claim 1, wherein the antigen is a bacterial antigen.
13. The composition of claim 1, wherein the APC stimulating agent is a CD40 agonist.
14. The composition of claim 13, wherein the CD40 agonist is an agonist antibody selected from FGK45, HM40-3, 3/23, 5C3, Mab-89, BE-1, EA5, and M3 monoclonal antibodies.

15. The composition of claim 1, wherein the composition induces an immunogenic activity that is at least 1 fold greater than if the same antigen is presented in the absence of the composition.

16. The composition of claim 1, further comprising a pharmaceutically acceptable carrier.

17. A composition comprising:
   a biocompatible porous micro- or nanostructure comprising silicon, a plurality of pores and wherein the structure has an emission spectrum whose wavelength of maximum intensity is about 500 to about 1000 nm and an excitation spectrum whose wavelength of maximum intensity is between about 290 to about 700 nm by single photon excitation or about 600 to about 1200 nm by two photon excitation;
   an antigen within the pores; and
   a targeting moiety linked or bound to the structure for targeting to an antigen presenting cell and activating the antigen presenting cells.

18. A method of evoking an immune response to an antigen in a subject comprising contacting the subject with a composition of claim 1.

19. A composition comprising:
   a biocompatible porous micro- or nanostructure comprising silicon, a plurality of pores and wherein the structure has an emission spectrum whose wavelength of maximum intensity is about 500 to about 1000 nm and an excitation spectrum whose wavelength of maximum intensity is between about 290 to about 700 nm by single photon excitation or about 600 to about 1200 nm by two photon excitation;
   an antigen within the pores; and
   a coating or encapsulating polymeric material that coats or encapsulates the biocompatible porous micro- or nanostructure, wherein the coating or encapsulating polymeric material further comprises an immune system activating agent.

* * * * *

UNITED STATES PATENT AND TRADEMARK OFFICE
CERTIFICATE OF CORRECTION

PATENT NO. : 9,394,369 B2  
APPLICATION NO. : 13/342889  
DATED : July 19, 2016  
INVENTOR(S) : Michael J. Sailor et al.

Page 1 of 1

It is certified that error appears in the above-identified patent and that said Letters Patent is hereby corrected as shown below:

In the Specification

Column 1, Line 13, please replace the paragraph as follows:
--STATEMENT AS TO FEDERALLY SPONSORED RESEARCH
This invention was made with government support under AI060536, CA124427, and CA119335 awarded by the National Institutes of Health. The government has certain rights in the invention.--

Signed and Sealed this  
Ninth Day of December, 2025

John A. Squires  
*Director of the United States Patent and Trademark Office*